United States Patent
Biver et al.

(10) Patent No.: US 10,730,855 B2
(45) Date of Patent: Aug. 4, 2020

(54) ELECTROCHROMIC COMPOUNDS AND OPTICAL ARTICLES CONTAINING THEM

(71) Applicant: Essilor International, Charenton-le-Pont (FR)

(72) Inventors: Claudine Biver, Charenton-le-Pont (FR); Fabien Berit-Debat, Charenton-le-Pont (FR); Samuel Archambeau, Charenton-le-Pont (FR); Christopher Gabbutt, Huddersfield (GB); Stuart Aiken, Huddersfield (GB); Bernard Mark Heron, Huddersfield (GB); Thomas David Broadbent, Huddersfield (GB)

(73) Assignee: Essilor International, Charenton-Le-Pont (FR)

( * ) Notice: Subject to any disclaimer, the term of this patent is extended or adjusted under 35 U.S.C. 154(b) by 0 days.

(21) Appl. No.: 16/471,050

(22) PCT Filed: Jan. 4, 2018

(86) PCT No.: PCT/EP2018/050218
§ 371 (c)(1),
(2) Date: Jun. 19, 2019

(87) PCT Pub. No.: WO2018/127540
PCT Pub. Date: Jul. 12, 2018

(65) Prior Publication Data
US 2019/0315718 A1    Oct. 17, 2019

(30) Foreign Application Priority Data
Jan. 9, 2017 (EP) ...................... 17150656

(51) Int. Cl.
*C07D 401/14* (2006.01)
*C09K 9/02* (2006.01)

(52) U.S. Cl.
CPC .............. *C07D 401/14* (2013.01); *C09K 9/02* (2013.01)

(58) Field of Classification Search
None
See application file for complete search history.

(56) References Cited

U.S. PATENT DOCUMENTS 10,563,120 B2 *  2/2020  Archambeau ......... G02F 1/1503
2016/0231635 A1    8/2016  Aiken et al.

FOREIGN PATENT DOCUMENTS

| EP | 2 848 667 A1 | 3/2015 | |
| JP | 2003-128654 A | 5/2003 | |
| WO | WO-03038508 A2 * | 5/2003 | ........... C07D 213/22 |

OTHER PUBLICATIONS

Zhang et al, ACS Applied Materials & Interfaces, 1(6), pp. 1250-1258 (Year: 2009).*
International Search Report dated Apr. 6, 2018 in PCT/EP2018/050218 filed Jan. 4, 2018, 4 pages.
Michio M. Matsushita, et al., "Metal Coordination Complexes Composed of Photo-Electrochemically Active Ligands" Molecular Crystals and Liquid Crystals Science and Technology. Section A. Molecular Crystals and Liquid Crystals, vol. 343, No. 1, XP055385063, Sep. 24, 2006; pp. 87-96 and cover page.

* cited by examiner

*Primary Examiner* — Zinna Northington Davis
(74) *Attorney, Agent, or Firm* — Oblon, McClelland, Maier & Neustadt, L.L.P.

(57) ABSTRACT

The present invention relates to a group of novel electrochromic compounds. More specifically, it relates to electrochromic compounds comprising one or several pyridinium rings and the use of these compounds as a variable transmittance medium for the manufacture of an optical article, such as an ophthalmic lens.

13 Claims, No Drawings

ELECTROCHROMIC COMPOUNDS AND OPTICAL ARTICLES CONTAINING THEM

The present invention relates to a group of novel electrochromic compounds. More specifically, it relates to electrochromic compounds comprising one or several pyridinium rings and the use of these compounds as a variable transmittance medium for the manufacture of an optical article, such as an ophthalmic lens.

Electrochromism is a well-known physical phenomenon which is observed with certain classes of chemical compounds that reversibly change colour when a voltage is applied to them. The material undergoes reversible changes in optical properties by oxidation and reduction. Advantageously, the electrochromic material is colourless when an electric field is not applied and becomes coloured when an electric field is applied.

An electrochromic device, i.e. a device containing electrochromic compounds, the absorbance of which depends only on the presence of an electric field, can thus have two states, i.e. a coloured state (when electrically activated) and a bleached state (in the inactive state). The optical transmission properties of the device depend on the nature of the electrochromic compounds.

There remains a need for improving electrochromic materials in order to use them as transparent media for forming high quality articles, in particular high quality ophthalmic lenses, while keeping electrochromic properties and having a wide range of colours.

Compounds comprising several pyridinium rings are known to be good candidates for electrochromic materials. The challenge with compounds comprising several pyridinium rings is that they may exhibit two reduction peaks, the second reduction process being known to generate species having solubility and/or stability issues. For example, bipyridinium (bipm) compounds may exhibit three oxidation states: $V^{2+}$ (bipm$^{2+}$), $V^+$ (bipm$^+$) and $V^0$ (bipm$^0$), as shown in the scheme below:

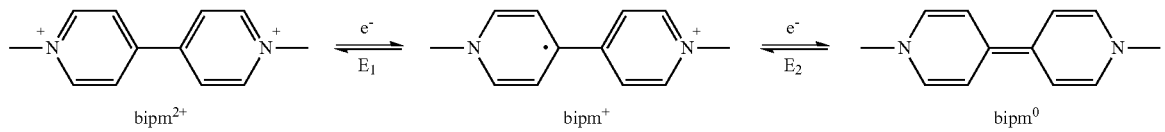

The reduction of $V^{2+}$ to $V^+$ occurs at potential $E_1$ and is reversible. However, the reduction of $V^+$ to $V^0$ that occurs at potential $E_2$ is often less reversible, in part because $V^0$ is frequently an insoluble species. Indeed, when $V^0$ is soluble it is known to be reactive, undergoing oxidation and participating in photochemical reactions to afford non-electrochromic impurities. Additionally, the species $V^0$ has a different visible absorption spectrum to $V^+$ which is problematic in variable transmission applications. Furthermore, the presence of $V^0$ leads to complications in electrochemical switching due to comproportionation reactions.

After conducting extensive research, the present inventors provide novel electrochromic compounds comprising one or several pyridinium groups that exhibit excellent electrochromic properties and that can be easily incorporated in a cell to form, for instance, an electrochromic lens. As such, the compounds of the present invention are advantageously:
- colourless in their inactivated state and coloured, for example red, pink, orange, yellow or brown, in their activated state;
- reversibly oxidized or reduced;
- easily activated, i.e. they have an electrochemical potential from −1.5 to −0.5 V;
- stable, i.e. no generation of degradation products (only one reversible oxidation/reduction peak or two peaks separated by at least 0.1V, preferably at least 0.3 V, more preferably at least 0.4 V, even more preferably at least 0.5 V).

The present invention thus relates to electrochromic compounds of formula (I) as defined below.

The present invention also relates to an electrochromic composition comprising at least one compound of formula (I).

Finally, the present invention relates to an electrochromic device, such as an ophthalmic lens, comprising an electrochromic compound of formula (I) or an electrochromic composition according to the invention.

Definitions

The expression "$C_6$-$C_{10}$ arylene" represents any divalent radical of an aromatic hydrocarbon comprising 6 to 10 carbon atoms. Examples of $C_6$-$C_{10}$ arylene groups include phenylene and naphthylene.

The expression "pyridinediyl radical" represents any divalent radical of a pyridine which is an aromatic group comprising 5 carbon atoms and a nitrogen.

The expression "pyridiniumdiyl radical" represents any divalent radical of a pyridinium which is an aromatic group comprising 5 carbon atoms and a positively charged nitrogen.

The expression "alkyl" represents any monovalent radical of a linear or branched hydrocarbon chain comprising 1 to 18 carbon atoms. The expression "$C_1$-$C_3$ alkyl" represents an alkyl group having 1 to 3 carbon atoms. The expression "$C_5$-$C_7$ alkyl" represents an alkyl group having 5 to 7 carbon atoms. Examples of $C_1$-$C_8$ alkyl groups include $C_1$-$C_3$ alkyl groups such as methyl, ethyl, n-propyl, i-propyl, $C_5$-$C_7$ alkyl groups such as n-pentyl, n-hexyl, 2,2-dimethylpropyl or n-heptyl.

The expression "alkoxy" represents a radical of formula —OR wherein R is a $C_1$-$C_{12}$ alkyl. Examples of $C_1$-$C_{12}$ alkoxy groups include $C_1$-$C_6$ alkoxy groups such as —OCH$_3$, —OCH$_2$CH$_3$ or —O(CH$_2$)$_5$CH$_3$.

The expression "alkylthio" represents a radical of formula —SR wherein R is a $C_1$-$C_{12}$ alkyl. Examples of $C_1$-$C_{12}$ alkylthio groups include —SCH$_3$ and —SCH$_2$CH$_3$.

The expression "haloalkyl" represents any $C_1$-$C_{12}$ alkyl group substituted by one or more halogen atom such as F or Cl. Examples of $C_1$-$C_{12}$ haloalkyl groups include $C_1$-$C_{12}$ perhaloalkyl groups, in particular $C_1$-$C_4$ perhaloalkyl groups such as —CF$_3$, as well as $C_1$-$C_{12}$ (perhaloalkyl)alkyl groups, in particular ($C_1$-$C_4$ perhaloalkyl)-($C_1$-$C_4$ alkyl) groups such as —CH$_2$CF$_3$.

The expression "haloalkoxy" represents a radical of formula —OR wherein R is a $C_1$-$C_{12}$ haloalkyl. Examples of $C_1$-$C_{12}$ haloalkoxy include $C_1$-$C_{12}$ perhaloalkoxy groups, in particular $C_1$-$C_4$ perhaloalkoxy groups such as —$OCF_3$, as well as $C_1$-$C_{12}$ (perhaloalkyl)alkoxy groups, in particular ($C_1$-$C_4$ perhaloalkyl)-($C_1$-$C_4$ alkoxy) groups such as —$OCH_2CF_3$.

The expression "haloalkylthio" represents a radical of formula —SR wherein R is a $C_1$-$C_{12}$ haloalkyl. Examples of $C_1$-$C_{12}$ haloalkoxy groups include $C_1$-$C_{12}$ perhaloalkylthio groups, in particular $C_1$-$C_4$ perhaloalkylthio groups such as —$SCF_3$, as well as $C_1$-$C_{12}$ (perhaloalkyl)alkylthio groups, in particular ($C_1$-$C_4$ perhaloalkyl)-($C_1$-$C_4$ alkylthio) groups such as —$SCH_2CF_3$.

The expression "polyalkylenoxy" represents a radical of formula —$O(R'O)_mR$ wherein R' is a $C_1$-$C_{12}$ alkylene, R is a $C_1$-$C_{12}$ alkyl and m is an integer from 1 to 12. Examples of poly($C_1$-$C_{12}$ alkylenoxy) groups include $OCH_2CH_2OCH_3$.

The expression "alkoxycarbonyl" represents a radical of formula —C(O)OR wherein R is a $C_1$-$C_8$ alkyl group. Examples of alkoxycarbonyl groups possessing a $C_1$-$C_8$ chain include —$C(O)OCH_3$ and —$C(O)OC_2H_5$.

The expression "aryl" represents any monovalent radical of an aromatic hydrocarbon comprising 6 to 18 carbon atoms. Examples of $C_6$-$C_{18}$ aryl groups include phenyl, naphthyl, anthracenyl and phenanthrenyl.

The expression "heteroaryl" represents any monovalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroaryl groups include furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridinyl, pyridiniumyl, N-alkylpyridiniumyl, quinolinyl, quinolinium, isoquinolinyl, isoquinolinium, pyridazinyl, cinnolinyl, phthalazinyl, pyrimidinyl, quinazolinyl, pyrazinyl and quinoxalinyl.

The expression "pyridinyl group" represents any radical of a pyridine.

The expression "pyridiniumyl group" represents any radical of a pyridinium which is an aromatic group comprising 5 carbon atoms and a positively charged nitrogen.

The expression "N-alkylpyridiniumyl group" represents any radical of a pyridinium which is an aromatic group comprising 5 carbon atoms and a positively charged nitrogen, said nitrogen being substituted by an alkyl group.

The expression "N-arylpyridiniumyl group" represents any radical of a pyridinium which is an aromatic group comprising 5 carbon atoms and a positively charged nitrogen, said nitrogen being substituted by an aryl group, preferably a phenyl group.

Unless mentioned otherwise, the groups and radicals defined hereinabove may be unsubstituted or substituted by one or more substituents such as, for example, halogen, alkyl, alkoxy, aryl, heteroaryl, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino.

The expression "Z is not simultaneously bound in position 4 of cycle A and in position 4 of cycle B" means that Z and Y of cycle A and Z and Y of cycle B are not simultaneously in para positions. In other words, in this expression Y defines position 1 on cycles A and B.

Electrochromic Compounds

The electrochromic compounds of the present invention have a central core (represented as Z in formula (I) below), which is either a pyridinediyl radical or a pyridiniumdiyl radical, onto which are branched two lateral pyridines or pyridiniums (which are represented as rings or cycles A and B in formula (I) below).

As such, the electrochromic compounds of the present invention are represented by formula (I):

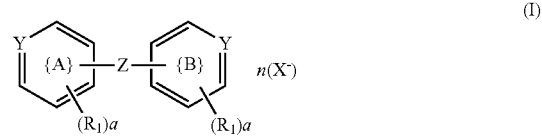

wherein:
Z is a pyridinediyl radical or a pyridiniumdiyl radical;
each Y is independently selected from N or ($^+$N—$R_2$)($X^-$) with $R_2$ a $C_1$-$C_8$ alkyl or $R_2$ an aryl group;
each one of $R_1$ is independently selected from H, alkyl, alkoxy, alkylthio, haloalkyl, haloalkoxy, haloalkylthio, polyalkylenoxy, alkoxycarbonyl, aryl, or heteroaryl;
n is 1, 2, 3 or 4;
a is 4;
$X^-$ is a counterion;
Z is not simultaneously bound in position 4 of cycle A and in position 4 of cycle B.

In the following, the ring nitrogen atom on the central core Z defines position 1.

In a first embodiment of the present invention, the central core Z of the compound of formula (I) is a pyridinediyl radical. Said pyridinediyl radical may be selected from:
2,3-branched pyridinediyl radical;
2,4-branched pyridinediyl radical;
2,5-branched pyridinediyl radical; or
2,6-branched pyridinediyl radical.

The terms "2,3-branched pyridinediyl radical", "2,4-branched pyridinediyl radical", "2,5-branched pyridinediyl radical" and "2,6-branched pyridinediyl radical" mean that the two lateral pyridines or pyridiniums (rings or cycles A and B) are branched on the central core (Z) in, respectively, positions 2 and 3, positions 2 and 4, positions 2 and 5 or positions 2 and 6 as represented below (optional substituents or fused systems on the central core are not shown):

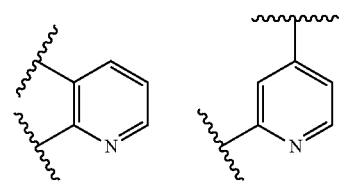 [SMILES: *c1cccnc1* ; *c1ccnc(*)c1]

"2,3-branched pyridinediyl radical" "2,4-branched pyridinediyl radical"

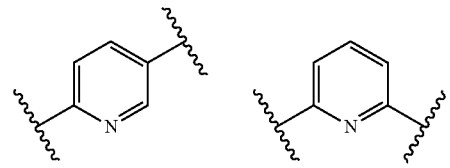 [SMILES: *c1ccc(*)nc1 ; *c1cccc(*)n1]

"2,5-branched pyridinediyl radical" "2,6-branched pyridinediyl radical"

In a second embodiment of the present invention, the central core Z of the compound of formula (I) is a pyridiniumdiyl radical. Said pyridiniumdiyl radical may be selected from:

1,2-branched pyridiniumdiyl radical;
1,4-branched pyridiniumdiyl radical;
2,3-branched N alkylpyridiniumdiyl radical;
2,4-branched N-alkylpyridiniumdiyl radical;
2,5-branched N-alkylpyridiniumdiyl radical;
3,4-branched N-alkylpyridiniumdiyl radical; or
3,5-branched N-alkylpyridiniumdiyl radical.

The terms "1,2-branched pyridiniumdiyl radical" and "1,4-branched pyridiniumyl radical" mean that the two lateral pyridines or pyridiniums (cycles A and B) are branched on the central pyridinium core (Z) in, respectively, positions 1 and 2 or positions 1 and 4 as represented below (optional substituents or fused systems on the central pyridinium core are not shown):

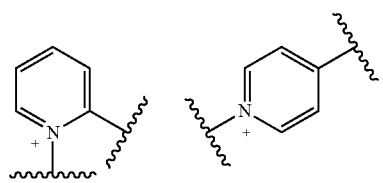

1,2-branched pyridiniumdiyl radical, 1,4-branched pyridiniumdiyl radical.

The terms "2,3-branched N-alkylpyridiniumyl radical", "2,4-branched N-alkylpyridiniumdiyl radical" and "2,5-branched N-alkylpyridiniumdiyl radical" mean that the two lateral pyridines or pyridiniums (cycles A and B) are branched on the central pyridinium core (Z) in, respectively, positions 2 and 3 or positions 2 and 4 or positions 2 and 5 as represented below (R is a alkyl group as defined above and optional substituents or fused systems on the central pyridinium core are not shown):

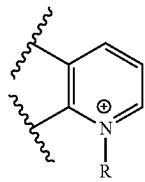

"2,3-branched N-alkylpyridiniumdiyl radical"

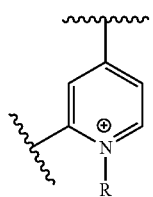

"2,4-branched N-alkylpyridiniumdiyl radical"

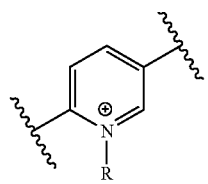

"2,5-branched N-alkylpyridiniumdiyl radical"

The terms "3,4-branched N-alkylpyridiniumdiyl radical" and "3.5 branched N-alkylpyridiniumdiyl radical" mean that the two lateral pyridines or pyridiniums (cycles A and B) are branched on the central pyridinium core (Z) in, respectively, positions 3 and 4 or positions 3 and 5 as represented below (R is a alkyl group as defined above and optional substituents or fused systems on the central pyridinium core are not shown):

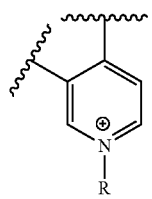

"3,4-branched N-alkylpyridiniumdiyl radical"

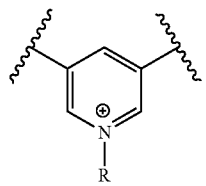

"3,5-branched N-alkylpyridiniumdiyl radical"

According to this second embodiment of the present invention, said pyridiniumdiyl radical is preferably selected from:

1,4-branched pyridiniumdiyl radical;
2,3-branched N-alkylpyridiniumdiyl radical; or
2,5 branched N-alkylpyridiniumdiyl radical.

When Z is a 1,4-branched pyridiniumdiyl radical, it is preferably substituted.

Preferably, said 1,4-branched pyridiniumdiyl radical is substituted by at least one aryl group. More preferably, said 1,4-branched pyridiniumdiyl radical is substituted by two aryl groups, even more preferably substituted by two methylphenyl ($-C_6H_4CH_3$) groups.

When Z is a 2,3-branched N-alkylpyridiniumdiyl radical, it is preferably an unsubstituted N-alkylpyridiniumdiyl radical.

When Z is a 2,5-branched N-alkylpyridiniumdiyl radical, it is preferably an unsubstituted N-alkylpyridiniumdiyl radical.

In a third embodiment of the present invention, the central core Z of the compound of formula (I) is as described above and each Y is N or ($^+$N—$R_2$)(X$^-$) with $R_2$ a $C_1$-$C_8$ alkyl or $R_2$ an aryl group. Preferably, Y is N or ($^+$N—$R_2$)(X$^-$) with $R_2$ a methyl, a n-hexyl or a substituted or an unsubstituted phenyl group.

When both Y are N, n is preferably equal to 1.

When at least one Y is (+N—R₂)(X⁻) with R₂ as defined above, n is preferably equal to 2, 3 or 4.

In a fourth embodiment of the present invention, Z and Y are as defined above and each one of $R_1$ is independently selected from H, alkyl, and heteroaryl, preferably selected from H, alkyl, pyridinyl group, pyridiniumyl group, N-alkylpyridiniumyl group or a N-arylpyridiniumyl group, preferably selected from H, $C_1$-$C_8$ alkyl a N—$C_1$-$C_{18}$ alkylpyridiniumyl group and a N-phenylpyridiniumyl group, more preferably selected from H, unsubstituted $C_1$-$C_3$ alkyl, a N—$C_5$-$C_7$ alkylpyridiniumyl group, a N—$C_1$-$C_2$ alkylpyridiniumyl group and an unsubstituted N-phenylpyridiniumyl group, even more preferably selected from H, methyl a N-methylpyridiniumyl group, a N-n-hexylpyridiniumyl group and an unsubstituted N-phenylpyridiniumyl group.

The counterion X⁻ may be any anion that maintains electric neutrality of the compounds of formula (I). X⁻ may be selected from halide, preferably fluoride and chloride, tetrafluoroborate, tetraphenylborate, hexafluorophosphate, nitrate, methanesulfonate, trifluoromethanesulfonate, toluenesulfonate, hexachloroantimonate, bis(trifluoromethanesulfonyl)imide, perchlorate, acetate and sulfate. Preferably, X⁻ is tetrafluoroborate.

Electrochromic compounds according to the invention are preferably well soluble in a solvent medium. Hence, electrochromic compounds preferably do not contain functional groups limiting solubility. In particular electrochromic compounds preferably do not contain a sulfonate group, a phosphonate group, a phosphate group, a phosphoric acid group, a trichlorosilyl group, a trialkoxysilyl group, a monochlorosilyl group, and a monoalkoxysilyl group.

In a fifth embodiment of the present invention, the electrochromic compounds are represented by formula (II):

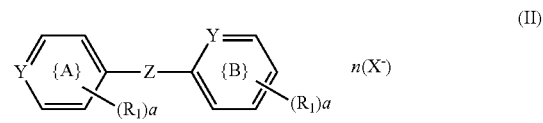

(II)

wherein Z, Y, $R_1$, X⁻, a and n are as defined above.

In a sixth embodiment of the present invention, the electrochromic compounds are represented by formula (III):

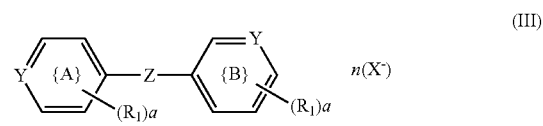

(III)

wherein Z, Y, $R_1$, X⁻, a and n are as defined above.

In a particularly preferred embodiment of the present invention, the compounds of the present invention are selected from the group consisting of:

| Compound | Structure |
|---|---|
| II-1 | 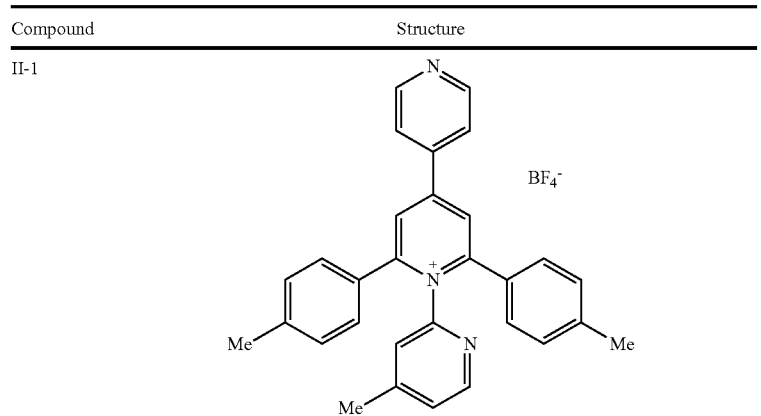 |
| II-2 | 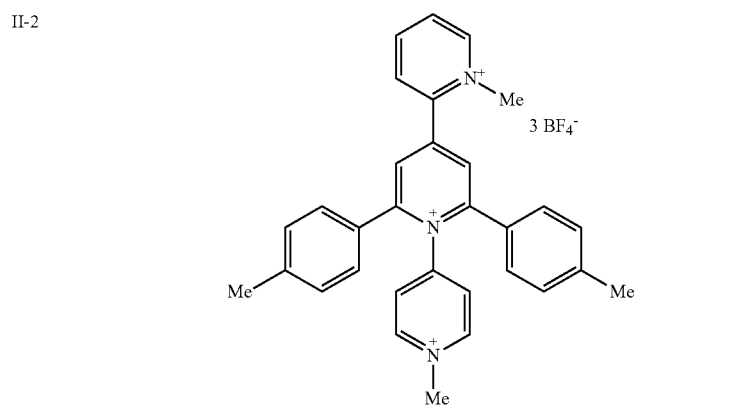 |

-continued
| Compound | Structure |
|---|---|
| II-3a | 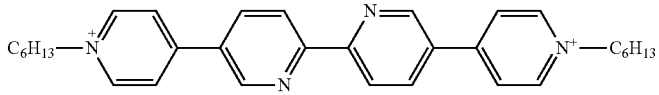 2 BF$_4^-$ |
| II-3b | 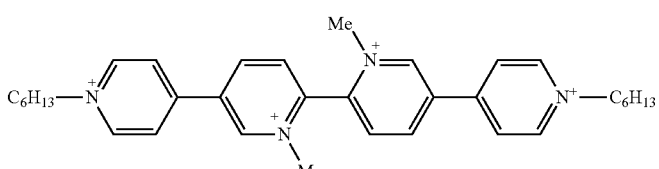 4 BF$_4^-$ |
| II-4 | 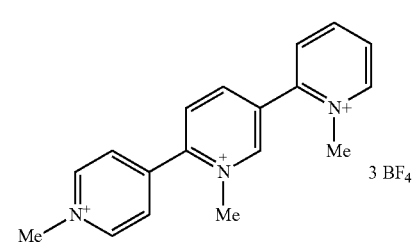 3 BF$_4^-$ |
| II-5 | 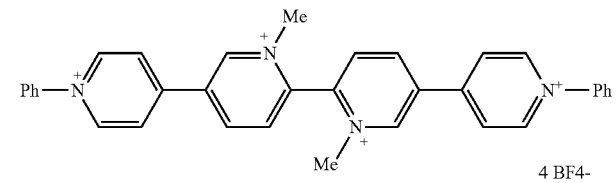 4 BF4- |
| III-1 | 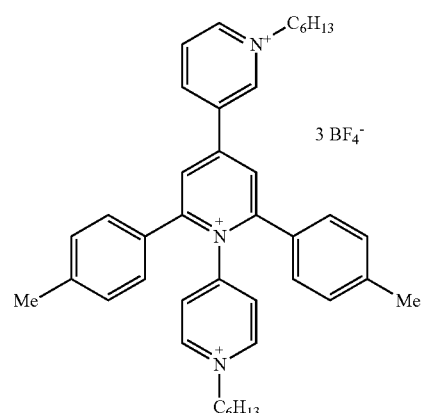 3 BF$_4^-$ |
| III-2 | 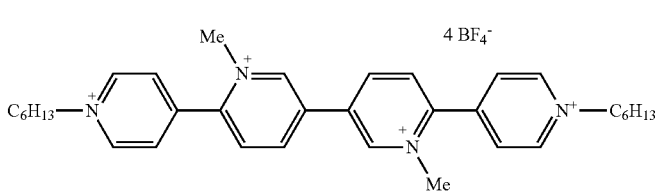 4 BF$_4^-$ |

-continued

| Compound | Structure |
|---|---|
| III-3 | 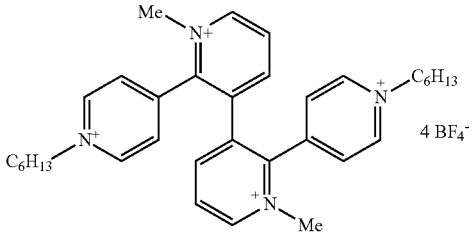 4 BF$_4^-$ |
| III-4 | 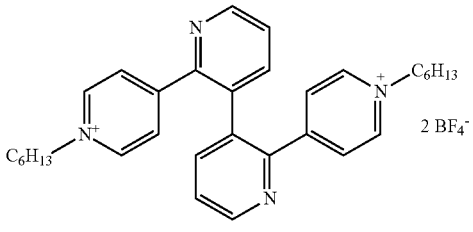 2 BF$_4^-$ |
| III-5 | 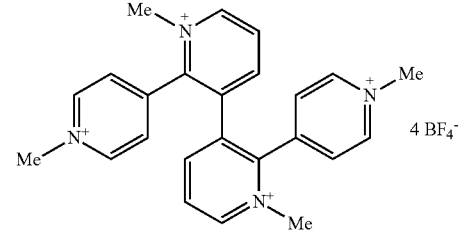 4 BF$_4^-$ |
| III-6 | 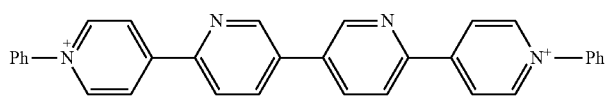 2BF4- |

Compounds of the present invention may be prepared according to various methods well known in the art.

Compounds having a pyridinium radical central core may be obtained by reacting the key intermediates, the pyrylogens Aa-Ac with 2-aminopyridine or 4-aminopyridine and their derivatives, according to the synthetic routes detailed in scheme 1. The pyrylogens A may be obtained by standard literature procedures that are known to those in the field (E. L. Clennan, C. Liao and E. Ayokosk, *J. Am. Chem. Soc.,* 2008, 130, 7552).

Scheme 1

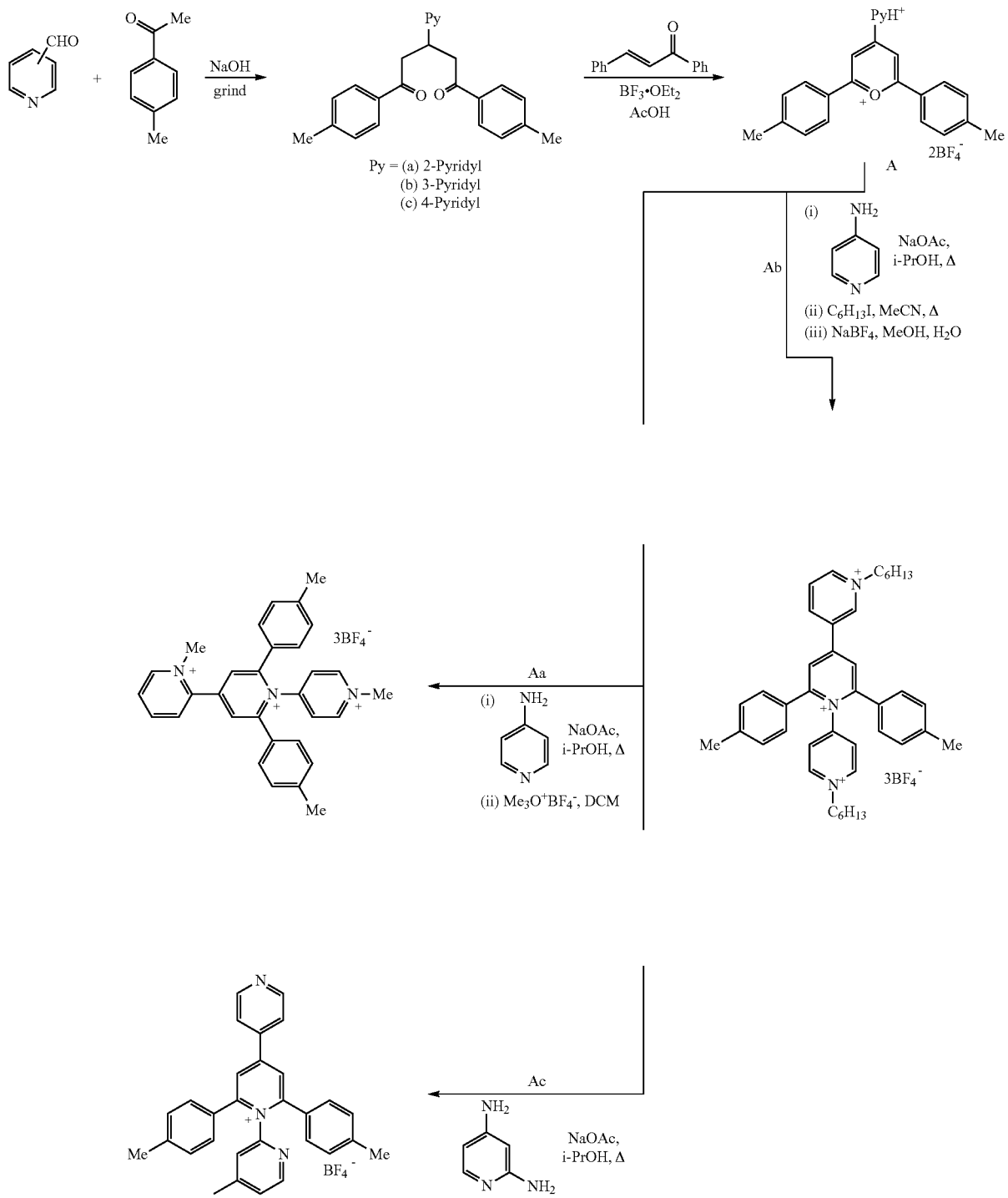

Compounds containing a quaterpyridine core may be obtained by the sequences shown in schemes 2-4. Thus the synthesis of the 4,2:5',3":6",4'''-quaterpyridine-1,1',1",1'''-tetraium species involved initial Suzuki-Miyaura coupling of 4-(4,4,5,5-tetramethyl-1,3,2-dioxaborolan-2-yl)pyridine with 2,5-dibromopyridine to give 5-bromo-2,4'-bipyridine (J. Sopkova-de Olivera Santos, A. S. Voisin-Chiret, G. Burzicki, L. Sebaoun, M. Sebban, J.-F. Lohier, R. Legay, H. Oulyadi, R. Bureau and S. Rault, *J. Chem. Inf Model.*, 2012, 52, 429) which was subjected to Ni-catalysed homocoupling (M. Tiecco, L. Testaferri, M. Tingoli, D. Chianelli and M. Montanucci, *Synthesis,* 1984, 736; M. Iyoda, H. Otsuka, K. Sato, N. Nisato and M. Oda, *Bull. Chem. Soc. Jpn.,* 1990, 63, 80) followed by sequential alkylation of 4,2:5',3":6",4'''-quaterpyridine as shown in scheme 2.

Scheme 2

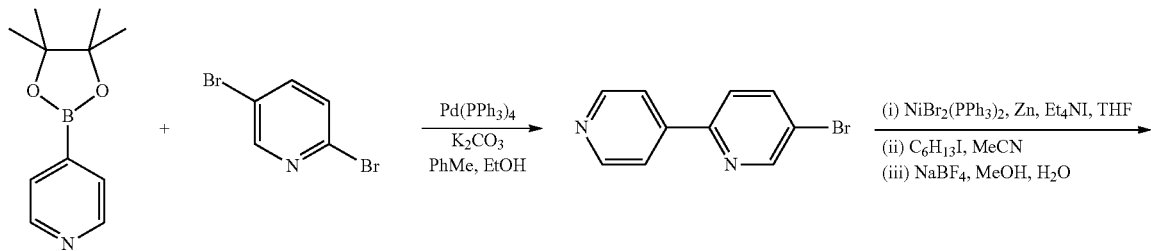

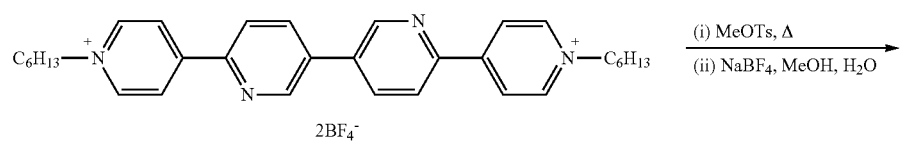

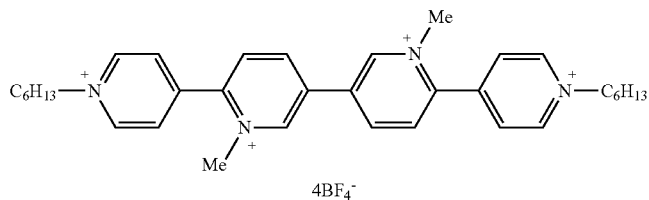

Suzuki-Miyaura coupling of 4-(4,4,5,5-tetramethyl-1,3,2-dioxaborolan-2-yl)pyridine to 2,3-dibromopyridine provided 3-bromo-2,4'-bipyridine that was converted by the standard procedures into the 4,2':3',3":2",4'''-quaterpyridine-1,1',1",1'''-tetraium salt (scheme 3).

Scheme 3

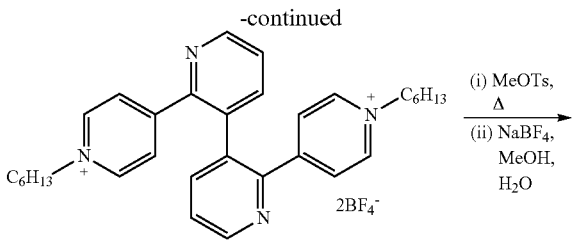

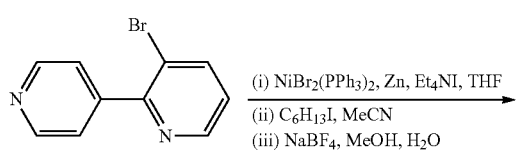

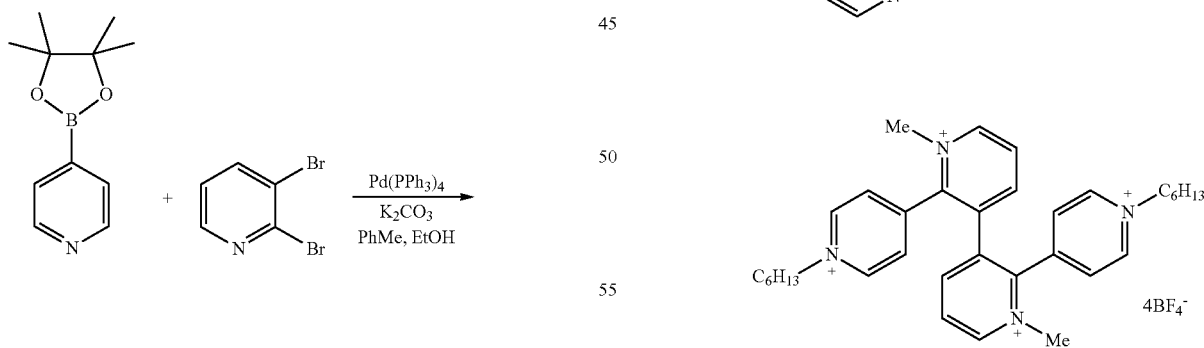

5-Bromo-2-iodopyridine was subjected to a Stille-Kelly coupling with hexa-n-butylditin to provide 5,5'-dibromo-2,2'-bipyridine (J. I. Bruce, J.-C. Chambron, P. Kolle and J.-P. Sauvage, *J. Chem. Soc., Perkin Trans. 1*, 2002, 1226; X.-L. Bai, X.-D. Liu, C.-Q. Kang and L.-X. Gao, Synthesis, 2005, 458.). A subsequent Suzuki-Miyaura coupling provided 4,3': 6',2":5",4'''-quaterpyridine that was converted to the tetra(N-alkyl) derivative in the usual manner (scheme 4).

Scheme 4

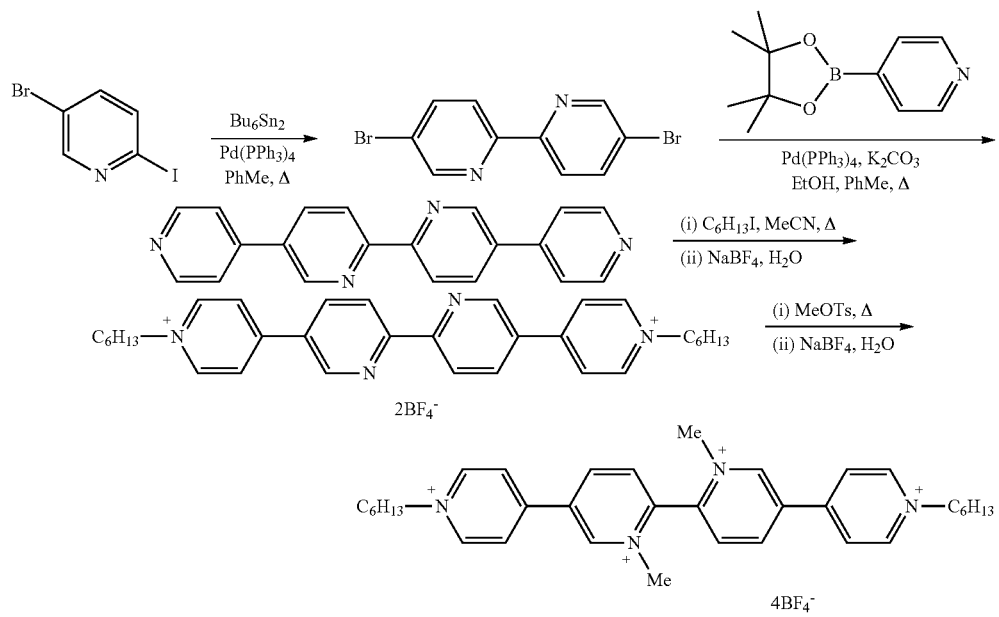

Selective N-arylation of both 4,2':5',3":6",4'''-quaterpyridine and the isomeric 4,3':6',2":5",4'''-quaterpyridine to give the 1,1'''-diphenyl-1,1'''-diium derivatives could be accomplished by Cu-mediated aryl transfer (T. Lv, Z. Wang, J. You, J. Lan and G. Gao, *J. Org. Chem.*, 2013, 78, 5723) from diphenyliodonium triflate. Subsequent methylation of the central bipyridine moieties was achieved by treatment with methyl tosylate by our standard procedure to generate the corresponding 1,1',1",1'''-tetraium derivatives. (scheme 5)

Scheme 5

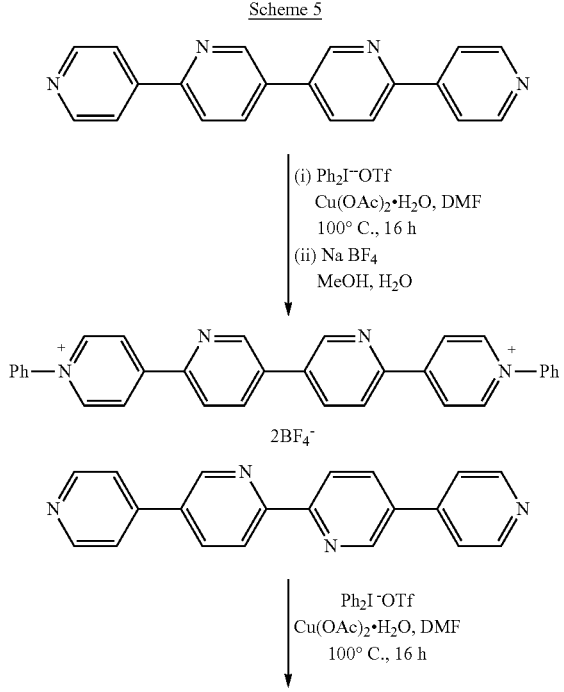

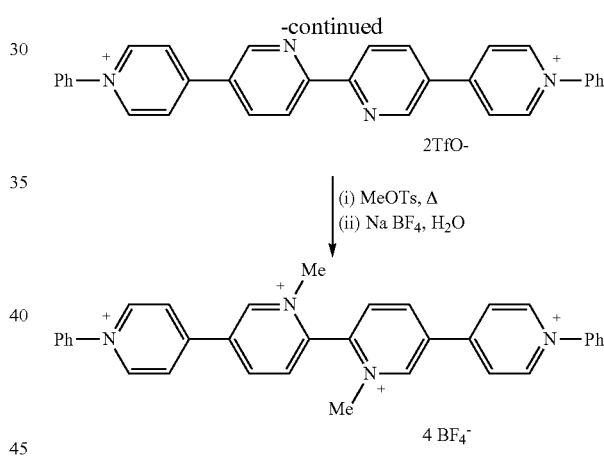

Electrochromic Composition

The present invention also relates to electrochromic compositions comprising at least one compound of formula (I), (II) or (III) as defined above as an oxidizing electrochromic compound. One or more additional oxidizing electrochromic compounds can be added to the composition of the invention so as to adapt the colour or the intensity of the coloured state of the composition. Said additional compound can be another compound of formula (I), (II) or (III) or a different compound such as compatible dyes or pigments. For example, the additional oxidizing electrochromic compound can be selected from alkylviologens, arylviologens, alkylarylviologens or anthraquinone and derivatives. Preferably, the additional compound has a redox potential close to the compound of formula (I), (II) or (III). Non limiting examples of additional oxidizing electrochromic compounds include the compounds described in applications WO 2015/040033 and WO 2015/040031.

The composition may also comprise at least one reducing compound. The reducing compound may also be an electrochromic compound. Example of reducing compounds include 5,10-dihydrophenazine, phenothiazine, phenoxazine, N,N,N',N'-tetramethyl-p-phenylenediamine, thioanthrene, tetrathiafulvalene, ferrocene and their derivatives.

The composition of the invention may comprise a host medium that may be a fluid, a mesomorphous medium or a gel. The host medium is introduced in the composition of the invention to dissolve the electrochromic compounds so as to form a solution of the electrochromic compounds. The host medium is preferably selected from the group consisting of organic solvents, liquid crystals, polymers, liquid crystal polymers and mixtures thereof.

Electrochromic compounds according to the invention are preferably well soluble in solvent medium. Hence, electrochromic compounds preferably do not contain functional groups limiting solubility. In particular electrochromic compounds preferably do not contain a sulfonate group, a phosphonate group, a phosphate group, a phosphoric acid group, a trichlorosilyl group, a trialkoxysilyl group, a monochlorosilyl group, and a monoalkoxysilyl group.

Examples of suitable organic solvents that can be used as host medium are redox-compatible solvents which cannot react with the electrochromic compounds of the composition, such as ethylene carbonate, propylene carbonate, γ-butyrolactone, γ-valerolactone, acetonitrile, propionitrile, benzonitrile, glutaronitrile, methylglutaronitrile, dimethylformamide, N-methylpyrrolidone, sulfolane, 3-methyl sulfolane, benzene, toluene, methyl ethyl ketone, acetone, ethanol, tetrahydrofurfuryl alcohol, 2-methoxyethyl ether, xylene, cyclohexane, 3-methylcyclohexanone, ethyl acetate, ethyl phenylacetate, tetrahydrofuran, methanol, methyl propionate, ethylene glycol, ethylene carbonate, ionic liquids, and mixtures thereof. Preference is given to carbonates and particularly propylene carbonate.

Examples of suitable liquid crystals that can be used as host medium are nematic or chiral nematic media.

Examples of suitable polymers that can be used as host medium are polymers which are soluble with the solvent, in particular PMMA or other acrylate polymers, polyurethane, polyethylene oxide, polypropylene oxide, polyvinyl acetate, poly(N-vinyl pyrrolidone), and polyvinylidene fluoride.

Examples of suitable liquid crystal polymers that may be used as host medium are Merck RM257 (Merck), LC242 (BASF) or SLM 90519 (Wacker). These liquid crystal polymers are generally used in combination with an organic solvent, for example one of the organic solvents mentioned above.

Electrochromic Device

The present invention also relates to an electrochromic device comprising a compound of formula (I), (II) or (III) as defined above or a composition according to the invention. Said device may be selected from an optical article, preferably an optical lens, or an optical filter, a window, preferably an aircraft window, a visor, a mirror, a head mounted device and a display, in particular a segmented or matrix display. Preferably, the device of the invention is an optical article, more preferably an optical lens, and even more preferably an ophthalmic lens.

Non limiting examples of head mounted devices include immersive and non-immersive devices, in particular see-through devices and see-around devices. Head mounted devices may be either augmented reality devices or virtual reality devices.

Non-limiting examples of ophthalmic lenses include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive, marine and aircraft windows, filters, shutters, and optical switches.

Preferably, the device of the invention comprises a mechanism for holding the compound or composition of the invention in a mechanically stable environment. More preferably, said device may comprise a pair of opposed substrates having a gap there between for receiving the mixture of the host medium and said compound or said composition of the present invention, and a frame for holding said pair of substrates adjacent one another.

The device of the present invention may thus comprise an optical component provided with at least one transparent cell arrangement juxtaposed in a parallel direction to the surface thereof, as disclosed in WO 2006/013250, each cell being tightly closed and containing at least one compound or composition of the present invention.

Other devices according to the invention can be devices as described in FR 2937154 or FR2950710 comprising at least one compound or composition of the invention.

EXAMPLES

This invention will be further illustrated by the following non-limiting examples which are given for illustrative purposes only and should not restrict the scope of the appended claims.

Example 1: Synthesis of 4-Methyl-2',6'-di-p-tolyl-[2,1':4',4"-terpyridin]-1'-ium tetrafluoroborate (II-1)

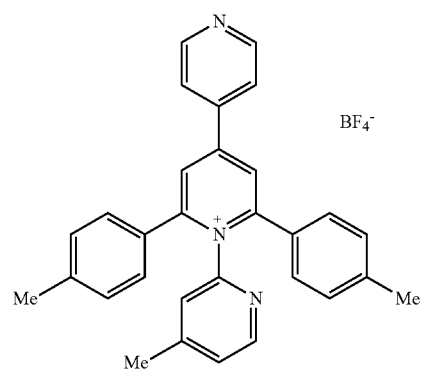

Ground NaOH (11.22 g, 200.5 mmol) was added portionwise to a mixture of 4'-methylacetophenone (37.6 g, 280 mmol) and pyridine-4-carboxaldehyde (15 g, 140 mmol) with grinding. The solid mass was suspended in hot EtOH/water (300 mL) with stirring. The resulting suspension was cooled and the solid collected by filtration and washed with water (50 mL). The solid was crystallised from hot EtOH, collected by filtration and washed with EtOH to give 3-(pyridin-4-yl)-1,5-di-p-tolylpentane-1,5-dione (28.46 g, 56%) as colourless needles.

Boron trifluoride etherate (48 mL) was added dropwise to a hot stirred solution of 3-(pyridin-4-yl)-1,5-di-p-tolylpentane-1,5-dione (12 g, 33.6 mmol) and trans-chalcone (7.27 g, 34.9 mmol) in AcOH under $N_2$. The resulting solution was heated at reflux for 6 h. The cooled solution was diluted with Et₂O (500 mL) and the solid collected by filtration and washed with Et₂O (2×100 mL) and air dried to give the 4-(pyridin-4-yl)-2,6-di-p-tolylpyrylium bis(tetrafluoroborate) (13.80 g, 80%) as an orange powder which was used directly in the next step.

A solution of 4-(pyridin-4-yl)-2,6-di-p-tolylpyrylium bis(tetrafluoroborate) (3 g, 5.8 mmol), 4-methylpyridin-2-amine (0.76 g, 7 mmol), NaOAc (1.92 g, 23.4 mmol) in propan-2-ol (45 mL) was heated at reflux for 16 h, cooled and water (200 mL) added. The aqueous propan-2-ol was decanted from the mixture, diluted with water (1.5 L) and filtered through celite. The foregoing celite was suspended in MeOH (50 mL), diluted with water (1.5 L) and filtered through celite. The aqueous propan-2-ol and the aqueous methanol phases were combined and evaporated under reduced pressure. The resulting residue was dissolved in MeOH (20 mL) and added dropwise to water at 0° C. with stirring. The resulting precipitate was collected by filtration, washed with water (10 mL) and air dried to give the 4-methyl-2',6'-di-p-tolyl-[2,1':4',4"-terpyridin]-1'-ium tetrafluoroborate (2.21 g, 73%) as a yellow powder. ¹H NMR 400 MHz (CD₃OD) δ 8.87 (2H, d, J=6.2 Hz), 8.60 (2H, s), 8.21 (1H, d, J=5.1 Hz), 8.15 (2H, d, J=6.2 Hz), 7.42-7.30 (5H, m), 7.26-7.16 (5H, m), 2.34 (6H, s) and 2.21 (3H, s); ¹³C NMR 100 MHz (CD₃OD) δ 157.22, 154.86, 151.51, 150.34, 148.14, 142.46, 141.26, 129.55, 129.47, 128.83, 126.44, 126.39, 124.72, 122.62, 19.90 and 19.24.

Example 2: Synthesis of 1,1"-Dimethyl-2',6'-di-p-tolyl-[2,4':1',4"-terpyridine]-1,1',1"-triium tris(tetrafluoroborate) (II-2)

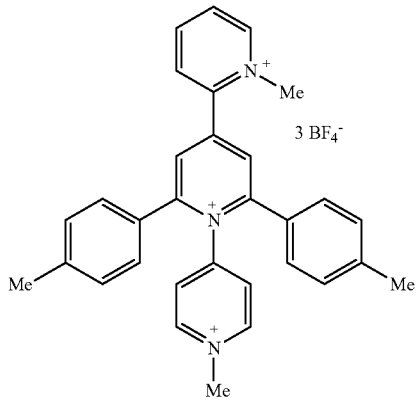

Sodium hydroxide (2 g, 50 mmol) in water (20 mL) was added to a stirred solution of pyridine-2-carboxaldehyde (5.4 g, 50.4 mmol) and 4'-methylacetophenone (13.4 g, 111 mmol) in EtOH (50 mL). The solution was stirred for 3 h, poured into water (100 mL) and the resulting precipitate collected by filtration and washed with water (100 mL). Crystallisation from EtOH (30 mL), gave the 3-(pyridin-2-yl)-1,5-di-p-tolylpentane-1,5-dione (6.95 g, 39%) as a cream powder.

BF₃.Et₂O (32 mL) was added dropwise to a refluxing solution of 3-(pyridin-2-yl)-1,5-di-p-tolylpentane-1,5-dione (6.87 g, 19.2 mmol) and trans-chalcone (4.53 g, 21.8 mmol) in AcOH (14 mL). Upon completion of the addition heating was continued for 6 h. The cooled mixture was diluted with Et₂O (200 mL) and the solid collected by filtration and washed with Et₂O (2×100 mL) and air dried. The foregoing solid was crystallised from AcOH (30 mL), collected by vacuum filtration and washed with Et₂O (2×50 mL) and air dried to give the 2-(2,6-di-p-tolylpyrylium-4-yl)pyridin-1-ium bis(tetrafluoroborate) (1.31 g, 68%) as a red powder which was used directly in the next step.

A solution of 2-(2,6-di-p-tolylpyrylium-4-yl)pyridin-1-ium bis(tetrafluoroborate) (1.30 g, 2.7 mmol), 4-aminopyridine (0.30 g, 3.2 mmol), NaOAc (0.88 g, 10.7 mmol) in propan-2-ol (25 mL) was heated at reflux for 16 h. The mixture was cooled to 60° C. and water (50 mL) was added. The resulting suspension was filtered through celite and the volume of the filtrate reduced. The resulting precipitate was collected by filtration, washed with water (2×10 mL) and air dried to give the 2',6'-di-p-tolyl-[2,4':1',4"-terpyridin]-1'-ium tetrafluoroborate (0.67 g, 50%) as a pale yellow powder.

A mixture of 2',6'-di-p-tolyl-[2,4':1',4"-terpyridin]-1'-ium tetrafluoroborate (1.61 g, 3.2 mmol) and Me₃OBF₄ (1.14 g, 7.7 mmol) in DCM (20 mL) was stirred under N₂ for 3 days. The mixture was then diluted with MeOH (20 mL) and filtered. The filtrate was thrice triturated with hot MeOH (20 mL) and the solid collected by filtration and air dried to give the 1,1"-dimethyl-2',6'-di-p-tolyl-[2,4': 1',4"-terpyridine]-1, 1',1"-triium tris(tetrafluoroborate) (1.45 g, 64%) as a pale yellow powder. ¹H NMR 400 MHz (d₆-AcMe) δ 9.43 (1H, bd, J=5.8 Hz), 9.23 (2H, bd, J=5.2 Hz), 9.06-8.94 (1H, m), 8.71 (1H, bd, J=1.9 Hz), 8.60-8.37 (4H, bm), 7.54 (4H, bd, J=7.0 Hz), 7.27 (4H, bd, J=7.0 Hz), 4.66 (3H, s), 4.58 (3H, s) and 2.34 (6H, s); ¹⁹F NMR 376 MHz (d₆-AcMe) δ −151.11; ¹³C NMR 100 MHz (d₆-AcMe) δ 157.56, 156.90, 152.61, 150.74, 149.02, 148.37, 147.72, 146.62, 142.08, 130.37, 130.29, 129.62, 129.36, 128.40, 128.28, 49.22, 47.96 and 20.52.

Example 3: Synthesis of 1,1'''-dihexyl-[4,3':6',2'':5'',4'''-quaterpyridine]-1,1'''-diium bis(tetrafluoroborate) (II-3a) and 1,1'''-Dihexyl-1',1''-dimethyl-[4,3':6',2'':5'',4'''-quaterpyridine]-1,1,1',1'',1'''-tetraium tetrakis(tetrafluoroborate) (II-3b)

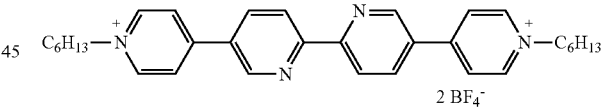

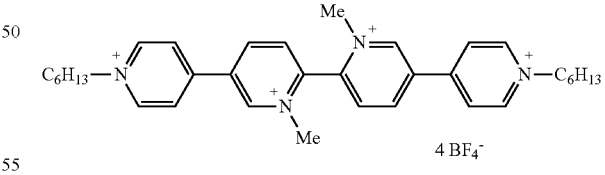

Aqueous HI (57%) was added to 2,5-dibromopyridine (12.60 g, 53.2 mmol) and NaI (11.40 g, 76 mmol). The resulting mixture was heated at reflux for 24 h, cooled and then diluted with water (100 mL). The resulting mixture was basified with NaHCO₃ and treated with Na₂S₂O₄ until colourless. The mixture was extracted with DCM (5×60 mL) and the dried (Na₂SO₄) solvent removed under reduced pressure. The residue was collected by filtration and washed with Et₂O (60 mL) and air dried to give the 5-bromo-2-iodopyridine (8.28 g, 55%) as a light grey powder. 5-Bromo-2-iodopyridine (6.60 g, 23.2 mmol) and Pd(PPh₃)₄ (0.72 g, 0.6 mmol) were dissolved in anhydrous PhMe (120 mL) under $N_2$. Hexa-n-butylditin (7.25 g, 12.5 mmol) was added and the solution heated at reflux for 3 days. The mixture was filtered through celite and the solvent removed. The residue was chromatographed on silica using a DCM to EtOAc gradient. The resulting residue was crystallised from EtOAc/hexanes to give the 5,5'-dibromo-2,2'-bipyridine (1.22 g, 33%) as a pale yellow powder. The crystallisation liquors were evaporated under reduced pressure and the residue dissolved in DCM, hexanes were added and the volume of solvent reduced. The resulting precipitate was collected by filtration and air dried to give a second crop of the product (0.46 g, 13%) as a cream powder.

A mixture of 4-(4,4,5,5-tetramethyl-1,3,2-dioxaborolan-2-yl)pyridine (2.38 g, 11.6 mmol), 5,5'-dibromo-2,2'-bipyridine (1.46 g, 4.6 mmol), $K_2CO_3$ (1.6 g, 11.6 mmol) and $Pd(PPh_3)_4$ (0.27 g, 5 mol %) in degassed EtOH (40 mL) and PhMe (40 mL) under $N_2$ was heated at reflux for 48 h. The mixture was cooled, diluted with water (200 mL) and poured into DCM (1.5 L) containing MeOH (150 mL) and filtered through celite. The foregoing celite was extracted with DCM (800 mL) and MeOH (100 mL) and the combined DCM and MeOH extracts were filtered through celite. The extraction/filtration sequence was repeated 3 further times. The organic phases were combined and filtered through celite once more whereupon the solvent was removed under reduced pressure and the residue triturated with hot acetone (100 mL). The triturated solid was collected by filtration and air dried to give the 4,3':6',2":5",4'''-quaterpyridine (1.18 g, 82%) as a light tan powder. The liquors were cooled and the precipitated solid collected by filtration to give a second crop of the product (0.15 g, 10%) as a pale pink powder.

A solution of 4,3':6',2":5",4'''-quaterpyridine (0.60 g, 1.9 mmol) and 1-iodohexane (2.46 g, 11.6 mmol) in MeCN (50 mL) in the dark under $N_2$ was heated at reflux for 24 h. Upon cooling the solid was collected by filtration and washed with $Et_2O$ (3×50 mL) and air dried to give the 1,1'''-dihexyl-[4,3':6',2":5",4'''-quaterpyridine]-1,1'''-diium diiodide (1.05 g, 74%) as a sandy powder. The liquors were diluted with $Et_2O$ (30 mL) and the precipitated solid collected by filtration and washed with $Et_2O$ (2×30 mL) and air dried to give a second crop of the product (0.11 g, 8%).

A filtered solution of 1,1'''-dihexyl-[4,3':6',2":5",4'''-quaterpyridine]-1,1'''-diium diiodide (1.00 g, 1.36 mmol) in hot MeOH (100 mL) was added dropwise to a solution of $NaBF_4$ (12 g, 109 mmol) in water (200 mL) with stirring. Stirring was continued for 0.5 h, then the resulting precipitate was collected by filtration and washed with water (2×10 mL). The foregoing solid was dissolved in hot MeOH (150 mL) and added dropwise to a solution of $NaBF_4$ (12 g, 109 mmol) in water (250 mL) with stirring. Stirring was continued for 0.5 h and then the resulting precipitate was collected by filtration, washed with water (2×10 mL) and air dried to give the 1,1'''-dihexyl-[4,3':6',2":5",4'''-quaterpyridine]-1,1'''-diium bis(tetrafluoroborate) (II-3a) (0.76 g, 85%) as a tan powder which was used directly in the subsequent step. $\delta_H$ 400 MHz (DMSO-$d_6$) 0.86 (6H, bt, 6.9 Hz), 1.21-1.39 (12H, m), 1.89-2.2 (4H, m), 4.61 (4H, t, J=7.2 Hz), 8.64-8.75 (8H, m), 9.20 (4H, d, J=6.6 Hz) and 9.45 (2H, bs); 8c 376 MHz (DMSO-$d_6$) −148.25−−148.13; $\delta_C$ 100 MHz (DMSO-$d_6$) 14.33, 22.36, 25.58, 31.07, 31.12, 60.72, 121.82, 125.42, 130.81, 137.73, 145.46, 149.67, 152.11 and 156.83.

A mixture of 1,1'''-dihexyl-[4,3':6',2":5",4'''-quaterpyridine]-1,1'''-diium bis(tetrafluoroborate) (0.56 g, 0.86 mmol) in methyl tosylate (3.18 g) was heated at 180° C. for 2.5 h. The cooled reaction mixture was triturated with $Et_2O$ (40 mL) and the solid collected by filtration and washed with $Et_2O$ (3×40 mL) and air dried. The foregoing solid was dissolved in methyl tosylate (1.71 g) and heated at 180° C. for 1 h. The cooled mixture was triturated with $Et_2O$ (4×30 mL), collected by filtration and air dried. The resulting gummy solid was dissolved in MeOH/water (25 mL, 1/4) and added dropwise to a solution of $NaBF_4$ (3.38 g, 30.7 mmol) in water (50 mL) with stirring. Stirring was continued for 0.5 h and the resulting precipitate was collected by filtration, washed with water (2×5 mL) and air dried. This solid was triturated with hot MeOH (8 mL) and the resulting solid collected by filtration and washed with cold MeOH (2 mL) to give the 1,1'''-dihexyl-1',1"-dimethyl-[4,3':6',2":5", 4'''-quaterpyridine]-1,1',1",1'''-tetraium tetrakis(tetrafluoroborate) (II-3b) (0.38 g, 51%) as a cream powder. $^1H$ NMR 400 MHz (CD$_3$OD/D$_2$O) δ 10.04-9.87 (2H, bs), 9.32 (2H, d, J=7.7 Hz), 9.13 (4H, d, J=6.3 Hz), 8.72-8.48 (6H, m), 4.70-4.54 (4H, m), 2.11-1.93 (4H, m), 1.50-1.17 (12H, m) and 0.82 (6H, t, J=6.7 Hz); $^{19}F$ NMR 376 MHz (CD$_3$OD/D$_2$O) δ −150.99.

Example 4: Synthesis of 1,1',1"-Trimethyl-[2,3':6', 4"-terpyridine]-1,1',1"-triium tris(tetrafluoroborate) (11-4)

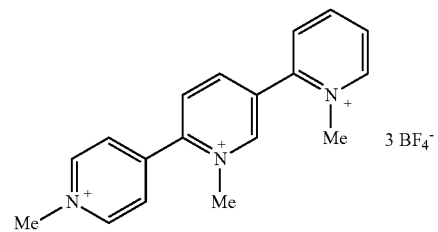

To a mixture of 2,5-dibromopyridine (5.92 g, 25 mmol), 4-(4,4,5,5-tetramethyl-1,3,2-dioxaborolan-2-yl)pyridine (5.13 g, 25 mmol), $Pd(PPh_3)_4$ (1.01 g, 0.88 mmol, 3.5 mol %), and $K_2CO_3$ (3.46 g, 25 mmol) under nitrogen was added degassed EtOH/PhMe (120 mL), and heated to reflux for 22 hours. The mixture was cooled, diluted with water (150 mL) and extracted with DCM (3×100 mL), dried with sodium sulfate and the solvent removed to give a tan solid. Purification by flash chromatography (5% MeOH/EtOAc), followed by recrystallisation from PhMe/hexane gave a low-density cream solid (2.78 g, 47.3%).

To a mixture of $Pd(PPh_3)_4$ (0.24 g, 0.21 mmol, 2.5 mol %) and 5-bromo-2,4'-bipyridine (1.97 g, 8.3 mmol) under nitrogen was added anhydrous THF (4.5 mL) and the slurry stirred for 0.5 h, after which 2-pyridylzinc bromide (25 mL, 12.5 mmol, 0.5 M in THF) was added slowly and heated to 65° C. for 3 hours. The mixture was cooled and HCl (15 mL, 2 M) added, made basic with NaOH (2.5 g in 25 mL) and a white precipitate observed. The forgoing mixture was then partitioned with $Et_2O$ (3×300 mL) and DCM (3×50 mL), the aqueous made basic and extracted with DCM (1×50 mL), dried with sodium sulfate, and the solvent removed in vacuo to give a brown solid. Purification by flash chromatography (1% MeOH/EtOAc) gave a cream powder.

A mixture of 2,3':6',4"-terpyridine (0.75 g, 3.22 mmol) and methyl tosylate (12.1 mL, 14.97 g, 80 mmol) under nitrogen was stirred at 180° C. for 4 hours, cooled, diethyl ether added and the precipitate collected by vacuum filtration, and washed with diethyl ether to give a grey solid (2.34 g, 91.8%).

From 1,1',1"-trimethyl-[2,3':6',4"-terpyridine]-1,1',1"-triium 4-methylbenzenesulfonate (2.20 g, 2.78 mmol), in a minimal amount of warm MeOH, and NaBF$_4$ (4.58 g, 41.7 mmol, 15.0 equiv.) in water (150 mL). Stirred for 0.5 h, NaBF$_4$ (15.0 equiv.) added, the solvent reduced in vacuo, the solution filtered through celite, NaBF$_4$ (15.0 equiv.) added and cooled to 4° C. for 16 h. The resulting precipitate was collected, and washed with a small amount of cold water to yield off-white crystals (0.86 g, 57.3%). mp: 300+° C. δ$_H$ (400 MHz DMSO-d$_6$) 9.61 (1H, s, Ar—H6), 9.36 (2H, d, J=6.4, Ar—H2',6'), 9.31 (1H, d, J=6.0 Hz, Ar—H6"), 9.10 (1H, d, J=1.2, 8.3 Hz, Ar—H4), 8.86 (1H, app. t, Ar—H4"), 8.51 (1H, d, J=8.3 Hz, Ar—H3), 8.46 (2H, d, J=6.3 Hz, Ar—H3',5'), 8.39 (1H, app. t, Ar—H5"), 8.20 (1H, d, J=7.6 Hz, Ar—H3"), 4.52 (3H, s, N—CH$_3$), 4.26 (6H, s, N',N"—CH$_3$).

Example 5: Synthesis of 1,1"-Dihexyl-2',6'-di-p-tolyl-[3,4':1',4"-terpyridine]-1,1',1"-triium tris(tetrafluoroborate) (III-1)

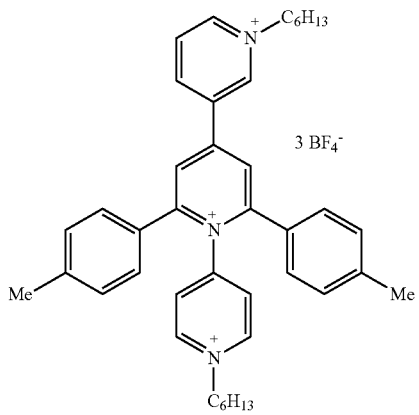

A mixture of pyridine-3-carboxaldehyde (5 g, 46.7 mmol) and 4'-methylacetophenone (12.52 g, 93.4 mmol) was added to ground NaOH (3.74 g, 93.5 mmol) in a pestle and mortar. Grinding was continued for 10 min and then the resulting mass was dissolved in hot EtOH (500 mL) and water (500 mL) was added. The mixture was cooled with stirring and the resulting precipitate was collected by filtration, washed with EtOH/water (50 mL, 1/1) and air dried to give the 3-(pyridin-3-yl)-1,5-di-p-tolylpentane-1,5-dione (12.38 g, 74%) as a colourless powder which was used without further purification.

BF$_3$.Et$_2$O (28 mL, 198 mmol) was added dropwise to a hot solution of 3-(pyridin-3-yl)-1,5-di-p-tolylpentane-1,5-dione (6 g, 16.8 mmol) and trans-chalcone (3.96 g, 19 mmol) in hot AcOH (13 mL) with stirring. The resulting solution was heated at reflux for 5 h and then cooled, diluted with Et$_2$O (400 mL) and the solid collected by filtration. The foregoing solid was crystallised from hot AcOH (40 mL), collected by filtration and then washed with AcOH (30 mL) then Et$_2$O (4×50 mL) and air dried to give the 3-(2,6-di-p-tolylpyrylium-4-yl)pyridin-1-ium bis(tetrafluoroborate) (5.38 g, 62%) as orange prisms which were used directly in the next step.

A solution of 3-(2,6-di-p-tolylpyrylium-4-yl)pyridin-1-ium bis(tetrafluoroborate) (2.00 g, 3.9 mmol), 4-aminopyridine (0.44 g, 4.7 mmol), NaOAc (1.28 g, 15.6 mmol) in propan-2-ol (40 mL) was heated at reflux for 16 h. The cooled reaction mixture was diluted with water (1.5 L) and filtered through celite. The residue obtained after removal of the aqueous propan-2-ol was dissolved in MeOH (10 mL) and added dropwise to a solution of NaBF$_4$ (2.57 g, 23.4 mmol) in water (200 mL) with stirring. Stirring was continued for 0.5 h and then the precipitate was collected by filtration, washed with water (2×10 mL) and air dried to give the 2',6'-di-p-tolyl-[3,4':1',4"-terpyridin]-1'-ium tetrafluoroborate (1.51 g, 77%) as a pale yellow powder.

A solution of 2',6'-di-p-tolyl-[3,4':1',4"-terpyridin]-1'-ium tetrafluoroborate (1.00 g, 2 mmol) and 1-iodohexane (5.06 g, 23.8 mmol) in MeCN (50 mL) under N$_2$ was heated at reflux in the dark for 5 days. The residue obtained upon removal of the cooled solvent was triturated with Et$_2$O (3×50 mL), collected by filtration and air dried to give the 1,1"-dihexyl-2',6'-di-p-tolyl-[3,4': 1',4"-terpyridine]-1,1',1"-triium tetrafluoroborate diiodide (1.83 g, 100%) as an ochre powder.

A solution of 1,1"-dihexyl-2',6'-di-p-tolyl-[3,4': 1',4"-terpyridine]-1,1',1"-triium tetrafluoroborate diiodide (1.50 g, 1.6 mmol) in MeOH (15 mL) was added dropwise to a solution of NaBF$_4$ (4.30 g, 39 mmol) in water (250 mL) with stirring. The volume of the solvent was reduced and the remaining solvent decanted from the residue. The foregoing residue was dissolved in MeOH (40 mL) and added dropwise to NaBF$_4$ (8.60 g, 78 mmol) in ice cold water (500 mL) with rapid stirring. The resulting precipitate was collected by filtration (maintaining ice cold temperature), washed with ice cold water (2×20 mL) and dried, cold, under vacuum to give the 1,1"-dihexyl-2',6'-di-p-tolyl-[3,4':1',4"-terpyridine]-1,1',1"-triium tris(tetrafluoroborate) (0.59 g, 43%) as a yellow powder. $^1$H NMR 400 MHz (CD$_3$OD) δ 9.77 (1H, s), 9.31-9.16 (2H, m), 9.14 (2H, d, J=6.3 Hz), 8.81 (2H, s), 8.40-8.29 (2H, m), 8.23 (2H, d J=6.3 Hz), 7.46 (4H, d, J=7.9 Hz), 7.28 (4H, d, J=7.9 Hz), 4.76 (2H, t, J=7.6 Hz), 4.58 (2H, t, J=6.8 Hz), 2.35 (6H, s), 2.21-2.03 (2H, m), 1.95-1.76 (2H, m), 1.57-1.21 (10H, m), 1.17-1.02 (2H, m) and 1.00-0.81 (6H, m); $^{19}$F NMR 376 MHz (CD$_3$OD) δ −153.35; $^{13}$C NMR 100 MHz (CD$_3$OD) δ 157.00, 152.75, 152.10, 146.97, 146.29, 145.05, 144.96, 142.40, 135.06, 130.14, 129.55, 128.54, 128.45, 128.28, 127.75, 62.58, 62.51, 31.03, 30.90, 30.71, 30.60, 25.53, 24.91, 22.07, 22.06, 20.04, 12.91, 12.88.

Example 6: Synthesis of 1,1'"-Dihexyl-1',1"-dimethyl-[4,2':5',3":6",4'"-quaterpyridine]-1,1',1",1'"-tetraium tetrakis(tetrafluoroborate) (III-2)

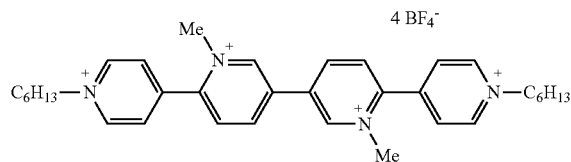

A mixture of 4-(4,4,5,5-tetramethyl-1,3,2-dioxaborolan-2-yl)pyridine (3.89 g, 19 mmol), 2,5-dibromopyridine (5 g, 21.1 mmol), K$_2$CO$_3$ (2.88 g, 20.1 mmol) and Pd(PPh$_3$)$_4$ (0.49 g, 2 mol %) in degassed EtOH (40 mL) and PhMe (40 mL) under N$_2$ was heated at reflux for 16 h. The cooled solution was poured into water (200 mL), extracted with DCM (3×100 mL) and the combined organic phases dried (Na$_2$SO$_4$) and the solvent removed under reduced pressure. The residue was chromatographed on silica using MeOH (1% in EtOAc) as eluent. The solvent was removed under reduced pressure to give the 5-bromo-2,4'-bipyridine (3.54 g, 79%) as an off white solid.

Under $N_2$, a mixture of $NiBr_2$ $(PPh_3)_2$ (3.03 g, 4.1 mmol, 30 mol %), Zn dust (1.32 g, 20.3 mmol) and $Et_4NI$ (3.49 g, 13.6 mmol) in THF (30 mL) was stirred for 0.5 h. A solution of 5-bromo-2,4'-bipyridine (3.19 g, 13.6 mmol) in THF (25 mL) was added and the mixture heated at 60° C. for 24 h. The cooled mixture was diluted with water (200 mL) and EtOAc (100 mL), filtered and the residue washed with EtOAc (50 mL). The residue was stirred with aq. ammonia (200 mL), extracted with DCM (5×200 mL), dried ($Na_2SO_4$) and the solvent removed under reduced pressure. The resulting residue was suspended in hot DCM (30 mL) and hexane (30 mL) was added. The mixture was cooled and the solid collected by filtration. The foregoing solid was dissolved in DCM (300 mL), washed with NaOH (2 M, 100 mL), dried ($Na_2SO_4$) and the solvent reduced and hexane added. The resulting precipitate was collected by filtration and washed with hexanes and air dried to give the 4,2':5',3":6",4'"-quaterpyridine (1.47 g, 70%) as a pale yellow powder. A solution of 4,2':5',3":6",4'"-quaterpyridine (0.89 g, 2.9 mmol) and 1-iodohexane (3.65 g, 17.2 mmol) in MeCN (50 mL) was heated at reflux for 24 h. The solid produced was collected by filtration and washed with $Et_2O$ (3×30 mL) and air dried to give the 1,1'"-dihexyl-[4,2':5',3":6",4'"-quaterpyridine]-1,1'"-diium diiodide (1.68 g, 80%) as an orange powder. The filtration liquors were diluted with $Et_2O$ (100 mL) and filtered to give a second crop of the product (0.41 g, 19%) as a light orange powder after washing with $Et_2O$ (2×30 mL).

A solution of 1,1'"-dihexyl-[4,2':5',3":6",4'"-quaterpyridine]-1,1'"-diium diiodide (1.61 g, 2.2 mmol) in warm MeOH/water (25 mL, 5/2) was added dropwise to $NaBF_4$ in water (200 mL) with stirring. Stirring was continued for 0.5 h and the mixture warmed to ensure dissolution of any solid. The solid which precipitated upon cooling was collected by filtration and washed with water (2×5 mL) and air dried to give the 1,1'"-dihexyl-[4,2':5',3":6",4'"-quaterpyridine]-1,1'"-diium bis(tetrafluoroborate) (1.31 g, 92%) as a yellow powder.

A solution of 1,1'"-dihexyl-[4,2':5',3":6",4'"-quaterpyridine]-1,1'"-diium bis(tetrafluoroborate) (0.94 g, 1.4 mmol) in methyl tosylate (3.21 g, 17.3 mmol) was heated at 180° C. for 1 h. The solid resulting from the cooled mixture was triturated with $Et_2O$ (3×30 mL) and collected by filtration to afford a cream powder (1.47 g). The foregoing solid was dissolved in warm MeOH (20 mL) and added dropwise to $NaBF_4$ (3.79 g, 34.4 mmol) in water (100 mL) with stirring. Stirring was continued for 0.5 h and the resulting precipitate was collected by filtration. Trituration of the precipitate with hot MeOH (20 mL), followed by cooling and filtration gave the 1,1'"-dihexyl-1',1"-dimethyl-[4,2':5',3":6",4'"-quaterpyridine]-1,1',1",1'"-tetraium tetrakis(tetrafluoroborate) (0.78 g, 63%) as a light grey powder. $^1H$ NMR 400 MHz ($d_6$-DMSO) δ 10.00 (2H, bs), 9.45 (4H, bd, J=5.8 Hz), 9.38 (2H, bd, J=8.2 Hz), 8.63-8.50 (6H, m), 4.77 (4H, bt, J=6.9 Hz), 4.33 (6H, s), 2.10-1.92 (4H, bm), 1.49-1.25 (12H, bm) and 1.00-0.82 (6H, bs); $^{19}F$ NMR 376 MHz ($d_6$-DMSO) δ −148.26; $^{13}C$ NMR 100 MHz ($d_6$-DMSO) δ 150.74, 147.08, 146.19, 146.08, 144.21, 133.34, 130.75, 129.44, 61.84, 48.59, 31.32, 31.09, 25.56, 22.36 and 14.34.

Example 7: Synthesis of 1,1'"-Dihexyl-[4,2':3',3": 2",4'"-quaterpyridine]-1,1'"-diium bis(tetrafluoroborate) (III-4)

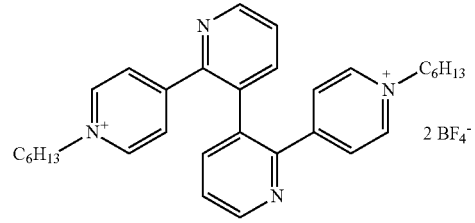

A mixture of 4-(4,4,5,5-tetramethyl-1,3,2-dioxaborolan-2-yl)pyridine (4.32 g, 21.1 mmol), 2,3-dibromopyridine (5 g, 21.1 mmol), $K_2CO_3$ (3.49 g, 25.3 mmol) and $Pd(PPh_3)_4$ (24 mg, 1 mol %) in degassed EtOH (30 mL) and PhMe (30 mL) under $N_2$ was heated at reflux for 7 days. The cooled mixture was poured into water (100 mL), extracted with DCM (3×100 mL), dried ($Na_2SO_4$) and the solvent removed under reduced pressure. The residue was chromatographed on silica using MeOH (0-3% in EtOAc) as eluent. Crystallisation of the resulting solid from hot EtOAc/hexanes gave the 3-bromo-2,4'-bipyridine (2.67 g, 54%) as pale orange needles. Evaporation of the crystallisation liquors gave a solid which was crystallised from DCM/hexanes to give a second crop of the product (0.59 g, 12%) as pale orange needles. Under $N_2$, a mixture of $NiBr_2(PPh_3)_2$ (3.01 g, 4 mmol, 30 mol %), Zn dust (1.31 g, 20.1 mmol) and $Et_4NI$ (3.44 g, 13.4 mmol) in THF (30 mL) was stirred for 0.5 h. A solution of 3-bromo-2,4'-bipyridine (3.15 g, 13.4 mmol) in THF (30 mL) was added and the mixture heated at 60° C. for 20 h. The cooled mixture was diluted with aq. ammonia (100 mL), extracted with DCM (4×100 mL). The combined DCM extracts were washed with water (50 mL), dried ($Na_2SO_4$) and the solvent removed under reduced pressure. The residue was chromatographed on silica using MeOH (0-5% in EtOAc) as eluent. The fraction with a Rf.=0.3 (EtOAc) was collected and the solvent removed under reduced pressure. The residue was crystallised from EtOAc/hexanes to give the 4,2':3',3":2",4'"-quaterpyridine (1.10 g, 53%) as a cream powder.

A solution of 4,2':3',3":2",4'"-quaterpyridine (0.79 g, 2.5 mmol) and 1-iodohexane (3.24 g, 15.3 mmol) in MeCN (50 mL) was heated at reflux for 24 h. On cooling the solvent was reduced to −10 mL and $Et_2O$ (50 mL) was added. The resulting precipitate was triturated with $Et_2O$ (3×50 mL), collected by filtration and air dried to give a tacky orange solid. The solid was dissolved in MeOH (5 mL) and added dropwise to a solution of $NaBF_4$ (11.20 g, 101.6 mmol) in water (100 mL) with stirring. The resulting solution was reduced in volume and filtered through fluted paper. The residue was dissolved in MeOH, poured into water (30 mL) and the solvent reduced in volume. The resulting gum was filtered through fluted paper and air dried. The gum was washed from the filter paper with methanol and the solvent removed to give the 1,1'"-dihexyl-[4,2':3',3":2",4'"-quaterpyridine]-1,1'"-diium bis(tetrafluoroborate) (1.05 g, 63%) as a yellow glass. $^1H$ NMR 400 MHz ($CD_3OD$) δ 8.93 (2H, dd, J=1.4 and 4.7 Hz), 8.76 (4H, d, J=6.7 Hz), 8.22 (2H, dd, J=1.4 and 7.9 Hz), 7.81 (2H, dd, J=4.7 and 7.9 Hz) and 7.66 (4H, d, J=6.7 Hz), 4.68-4.50 (4H, m), 2.09-1.90 (4H, m), 1.47-1.30 (12H, m) and 1.02-0.86 (6H, m); $^{19}F$ NMR 376 MHz ($CD_3OD$) δ −153.67; $^{13}C$ NMR 100 MHz (CD$_3$OD) δ 154.80, 150.83, 150.27, 144.50, 140.72, 133.43, 127.59, 125.97, 61.46, 30.83, 30.77, 25.48, 22.07 and 12.84.

Example 8: Synthesis of 1,1'''-Dihexyl-1',1''-dimethyl-[4,2':3',3'':2'',4'''-quaterpyridine]-1,1',1'',1'''-tetraium tetrakis(tetrafluoroborate) (III-3)

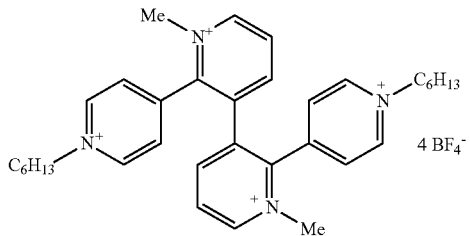

A solution of 1,1'''-dihexyl-[4,2':3',3'':2'',4'''-quaterpyridine]-1,1'''-diium bis(tetrafluoroborate) (0.94 g, 1.4 mol) in methyl tosylate (2.14 g, 11.5 mmol) was heated at 180° C. for 2 h. The solid resulting from the cooled mixture was triturated with Et$_2$O (4×30 mL) and collected by filtration to afford the 1,1'''-dihexyl-1',1''-dimethyl-[4,2':3',3'':2'',4'''-quaterpyridine]-1,1',1'',1'''-tetraium tetrafluoroborate tosylate (1.57 g, 99%) as an off white hygroscopic powder. A solution of 1,1'''-dihexyl-1',1''-dimethyl-[4,2':3',3'':2'',4'''-quaterpyridine]-1,1',1'',1'''-tetraium tetrafluoroborate tosylate (1.31 g, 1.2 mmol) in hot MeOH/H$_2$O (30 mL, 1/1) was added dropwise to a solution of NaBF$_4$ (5.19 g, 47.2 mmol) in water (30 mL) with stirring. The resulting mixture was heated to dissolution and cooled to 3° C. The resulting precipitate was collected by filtration and the solid triturated with hot MeOH (20 mL). The triturated solid was collected by filtration and washed with MeOH (5 mL) and air dried to give the 1,1'''-dihexyl-1',1''-dimethyl-[4,2':3',3'':2'',4'''-quaterpyridine]-1,1',1'',1'''-tetraium tetrakis(tetrafluoroborate) (0.52 g, 52%) as a colourless powder. $^1$H NMR 400 MHz (CD$_3$OD) δ9.26-9.14 (6H, m), 8.78 (2H, d, J=8.0 Hz), 8.41 (2H, dd, J=1.6 and 6.3 Hz), 8.31 (2H, dd, J=6.2 and 8.2 Hz), 8.00 (2H, dd, J=1.7 and 6.2 Hz), 4.69 (4H, t, J=7.9 Hz), 4.09 (6H, s), 2.19-1.98 (4H, m), 1.53-1.26 (12H, m) and 1.00-0.83 (6H, m); $^{19}$F NMR 376 MHz (CD$_3$OD) δ −151.90; $^{13}$C NMR 100 MHz (CD$_3$OD) δ 149.88, 148.22, 148.14, 147.27, 144.05, 133.35, 129.27, 129.08, 129.07, 63.03, 30.59, 30.44, 25.36, 21.90 and 13.10.

Example 9: Synthesis of 1,1',1'',1'''-Tetramethyl-[4,2':3',3'':2'',4'''-quaterpyridine]-1,1',1'',1'''-tetraium tetrakis(tetrafluoroborate) (III-5)

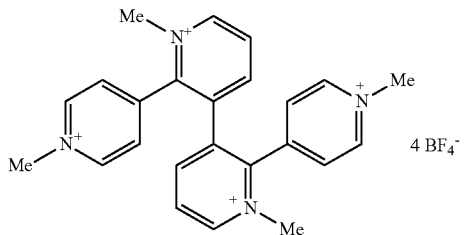

A mixture of 4,2':3',3'':2'',4'''-quaterpyridine (0.30 g, 0.97 mmol) and methyl tosylate (4.36 g, 23.3 mmol) was stirred under nitrogen at 180° C. for 4 hours. The cooled mixture was diluted with Et$_2$O and the solid was collected by filtration and washed sequentially with Et$_2$O, DCM, and Et$_2$O to give the 1,1',1'',1'''-tetramethyl-[4,2':3',3'':2'',4'''-quaterpyridine]-1,1',1'',1'''-tetraium tetrakis(4-methylbenzenesulfonate) (650 mg, 63.7%) as a grey powder. A filtered solution of 1,1',1'',1'''-tetramethyl-[4,2':3',3'':2'',4'''-quaterpyridine]-1,1',1'',1' tetraium tetrakis(4-methylbenzenesulfonate) (0.60 g, 0.57 mmol) in warm MeOH (15 mL) was added to a stirred solution of NaBF$_4$ (2.00 g, 18.2 mmol) in water (40 mL). The mixture was stirred for 30 minutes and then the 1,1',1'',1'''-tetramethyl-[4,2':3',3'':2'',4'''-quaterpyridine]-1,1',1'',1'''-tetraium tetrakis(tetrafluoroborate) (360 mg) was obtained as a grey powder by filtration. The filtrate was stirred at 60° C. for 15 minutes, cooled to 3° C., and left overnight. The volume of the filtrate was reduced in vacuo, the solution cooled to 3° C. for 1 hour, then filtration gave a second crop of the product (50 mg, 0.41 g, 99.9% overall) as a grey powder. $^1$H NMR 400 MHz (d$_6$-DMSO) δ 9.34 (2H, d, J=5.9 Hz), 9.20 (2H, d, J=6.3 Hz), 9.10 (2H, d, J=6.3 Hz), 8.64 (2H, d, J=7.7 Hz), 8.31-8.37 (4H, m), 7.80 (2H, dd, J=6.26 and 1.78 Hz), 4.43 (6H), 3.96 (6H, s); $^{13}$C NMR 100 MHz (d$_6$-DMSO) δ 149.15, 148.67, 148.30, 147.71, 147.52, 143.74, 133.47, 129.64, 129.12, 128.33, 48.95 and 48.90.

Example 10: Synthesis of 1,1'''-diphenyl-[4,2':5',3'':6'',4'''-quaterpyridine]-1,1'''-diium bis(tetrafluoroborate) (III-6)

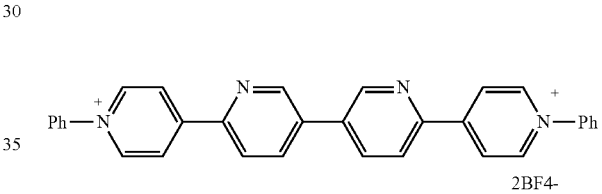

A mixture of 4,2':5',3'':6'',4'''-quaterpyridine (0.24 g, 0.8 mmol), diphenyliodonium triflate (1.00 g, 2.3 mmol), Cu(OAc)$_2$.H$_2$O (15.5 mg, 0.077 mmol, 10 mol %) in dry DMF (30 mL) was heated at 100° C. for 16 h; after cooling the solvent was removed under reduced pressure. The residue was triturated with Et$_2$O (2×20 mL) to give 1,1'''-diphenyl-[4,2':5',3'':6'',4'''-quaterpyridine]-1,1'''-diium ditriflate (0.54 g, 91%) as a light tan powder; δ$_H$ 400 MHz [(CD$_3$)$_2$CO] 7.75-7.86 (6H, m), 7.92-8.02 (4H, m), 8.77 (2H, dd, J=2.1 and 8.3 Hz), 8.83 (2H, d, J=8.3 Hz) 9.05 (4H, d, J=6.8 Hz), 9.51 (4H, d, J=6.8 Hz) and 9.54 (2H, d, J=2.1 Hz); δ$_F$ 376 MHz [(CD$_3$)$_2$CO]-77.56; δ$_C$ 100 MHz [(CD$_3$)$_2$CO] 121.14 (q, J=321 Hz, CF$_3$), 124.48, 124.68, 125.15, 130.73, 131.79, 134.55, 137.14, 142.89, 145.87, 149.80, 150.01 and 153.25.

A solution of 1,1'''-diphenyl-[4,2':5',3'':6'',4'''-quaterpyridine]-1,1'''-diium ditriflate (0.55 g, 0.72 mmol) in hot MeOH-water (1:1, 60 mL) was filtered through a glass wool plug and added dropwise to a solution of NaBF$_4$ (3.17 g, 28.8 mmol) in water (50 mL) with stirring. Stirring was continued for 0.5 h and the resulting precipitate filtered, washed with water (2×5 mL) and air dried to give 1,1'''-diphenyl-[4,2':5',3'':6'',4'''-quaterpyridine]-1,1'''-diium bis(tetrafluoroborate) (0.46 g, 100%) as a light tan powder; δ$_H$ 400 MHz (DMSO-d$_6$) 7.72-7.87 (6H, m), 7.92-8.03 (4H, m), 8.77 (2H, br.dd, J=1.8 and 8.2 Hz), 8.83 (2H, d, J=8.2 Hz), 9.05 (4H, d, J=6.7 Hz), 9.50 (2H, d, J=6.7 Hz) and 9.54 (2H, d, J=1.8 Hz); δ$_F$ 376 MHz (DMSO-d$_6$) −148.22 and −148.17.

Example 11: Synthesis of 1,1'''-diphenyl-[4,3':6',2'':5'',4'''-quaterpyridine]-1,1'''-diium tetrakis(tetrafluoroborate) (11-5)

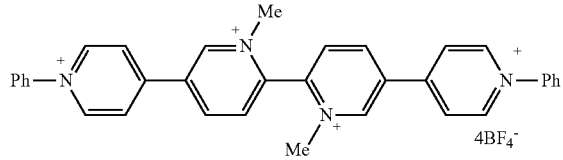

A mixture of 4,3':6',2'':5'',4'''-quaterpyridine (0.48 g, 1.55 mmol), diphenyliodonium triflate (2.00 g, 4.6 mmol), Cu(OAc)$_2$·H$_2$O (31 mg, 0.155 mmol, 10 mol %) in dry DMF (50 mL) was heated at 100° C. for 16 h; after cooling the solvent removed under reduced pressure. The residue was triturated with Et$_2$O (3×20 mL) and then with acetone (10 mL) to give 0.6 g of the crude ditriflate as a yellow powder. The latter was added to methyl tosylate (3 mL) and the mixture heated at 180° C. for 2 h; after cooling the mixture was triturated with Et$_2$O (3×20 mL). The resulting solid was dissolved in MeOH (20 mL). This solution was filtered through a glass wool plug and added dropwise to a solution of NaBF$_4$ (3.41 g, 31 mmol) in water (50 mL) with stirring. Stirring was continued for 0.5 h and the resulting precipitate collected by filtration, washed with water (3×5 mL) and air dried to give 1,1'''-diphenyl-[4,3':6',2'':5'',4'''-quaterpyridine]-1,1'''-diium tetrakis(tetrafluoroborate) (0.48 g, 37%) as a grey powder; $\delta_H$ 400 MHz (DMSO-d$_6$) 4.35 (6H, s), 7.80-7.91 (6H, m), 7.97-8.05 (4H, m), 8.79 (2H, d, J=8.3 Hz), 8.94 (4H, d, J=7.0 Hz), 9.68 (2H, dd, J=1.5 and 8.0 Hz), 9.78 (4H, d, J=7.0 Hz) and 10.36 (2H, br.s); $\delta_F$ 376 MHz (DMSO-d$_6$) −148.38−−148.06 (m); $\delta_C$ 100 MHz (DMSO-d$_6$) 48.57, 125.30, 126.11, 130.78, 131.45, 132.12, 135.60, 142.73, 144.31, 145.97, 146.59, 148.45 and 149.66.

Evaluation of Oxido-Reduction Potentials and Absorption Spectra of the Compounds of the Invention Method for Measuring Oxido-Reduction Potentials The oxido-reduction potentials of the compounds are measured by cyclic voltammetry with 3 electrodes.

The 3 electrodes used are:
1 Platinum working electrode
1 Platinum auxiliary or counter electrode
1 Platinum reference electrode which is immersed into a solution constituted of 0.01 M AgNO$_3$+0.1 M TBAP (tetrabutylammonium perchlorate) in acetonitrile.

The scan rate of the potential is fixed to 100 mV/s.

$E_1^{red}$ corresponds to the first reduction peak of the analysed compound.

$E_2^{red}$ corresponds to the second reduction peak of the analysed compound.

$E_1^{1/2}$ corresponds to the oxido-reduction potential of an oxidant/reductor system as calculated below:

$$E_1^{1/2}=(E_1^{red}+E_1^{ox})/2$$

wherein $E^1_{ox}$ corresponds to the first oxidation peak of the analyzed compound.

$\Delta E^{red}$ corresponds to the difference between $E_1^{red}$ and $E_2^{red}$ as calculated below:

$$\Delta E^{red}=|E_2^{red}|-|E_1^{red}|.$$

The indicated potential values are the first reduction potentials for the compounds, with respect to the standard hydrogen reference electrode (SHE).

The analysed solution comprises 0.005 M of the compound to be analysed and 0.5 M of TBAP salt in propylene carbonate as solvent.

Method for Measuring Absorption Spectra

The absorption spectra of the compounds are measured with a solution comprising 0.01 M of the compound to be analysed, 0.005 M of 10-methylphenothiazine (Mephtz) and 0.5 M of TBAP salt in propylene carbonate as solvent.

This solution is introduced into a quartz cell with optical path of 1 mm where a Platinum gauze working electrode (80 mesh) is placed in order to colour the analyzed compound on this electrode. A Platinum auxiliary (or counter electrode) and a Platinum reference electrode (immersed into a solution constituted of 0.01 M AgNO$_3$+0.1 M TBAP (tetrabutylammonium perchlorate) in acetonitrile) are also introduced in the quartz cell.

The absorption spectrum of the compound in the time domain is measured by a spectrophotometer.

For activating the compounds, the potential between the working electrode and the reference electrode, is increased, in absolute value, up to $E^1_{red}$ of the compound at a scanning speed of 1 mV/S.

The absorption spectrum is registered at this value of $E^1_{red}$. The $\lambda_{max}$ value corresponds to the maximum absorption peak within the visible spectrum (between 370 and 800 nm).

The results for each of the synthesized compounds are indicated in the Tables below. $E^1_{red}$ corresponds to the first reduction potential. The colour indicated in the Tables below is the visual colour perceived by emmetropic eyes under day light conditions. It should be noted that the $\lambda_{max}$ value just gives an approximate indication of the colour of a particular compound. However, as a consequence of the broad nature of the absorption bands, the whole absorption spectrum has to be taken into account in order to understand the final perceived colour of any one compound.

| Compound | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| II-1 | 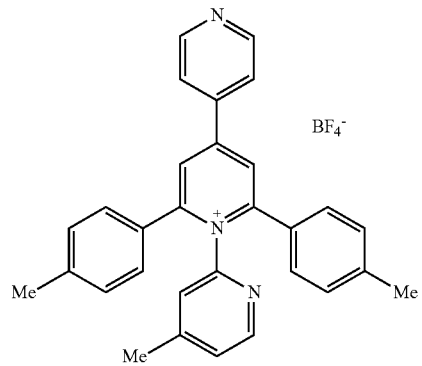 | −1.17 | −1.35 | 0.18 | −1.13 | 411/550 | pink/red |

-continued
| Compound | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| II-2 | 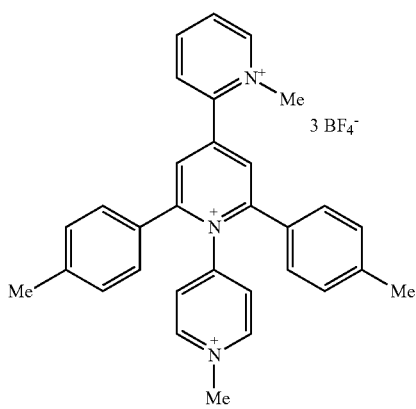 | −0.60 | * | * | −0.56 | 532 | red |
| II-3a | 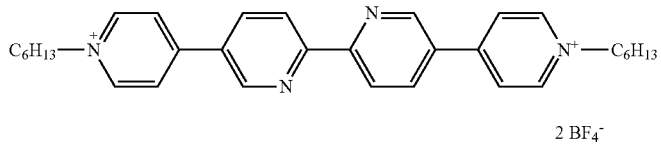 | −1.27 | * | * | −1.22 | 421 | yellow |
| II-3b | 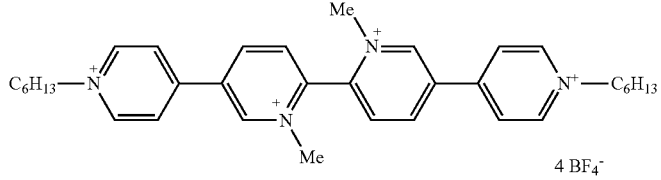 | −0.72 | * | * | * | 420 | yellow |
| II-4 | 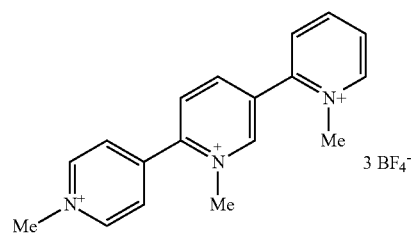 | −0.80 | * | * | * | 500 | red |
| II-5 | 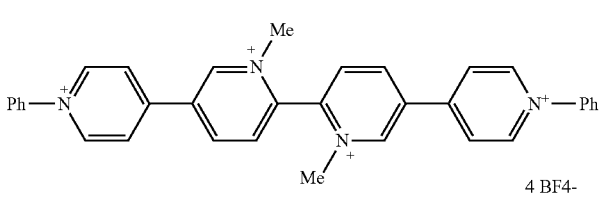 | −0.63 | * | * | −0.61 | 436 | orange |

-continued
| Compound | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| III-1 | 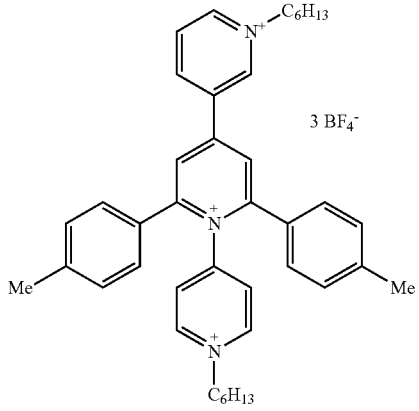 | −0.76 | * | * | −0.73 | 476 | brown |
| III-2 | 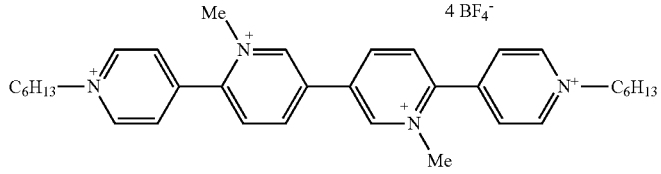 | −0.85 | −1.26 | 0.39 | −0.82 | 409 | brown |
| III-3 | 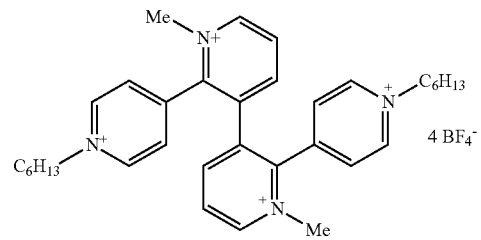 | −0.94 | −1.39 | 0.45 | * | 390 | orange |
| III-4 | 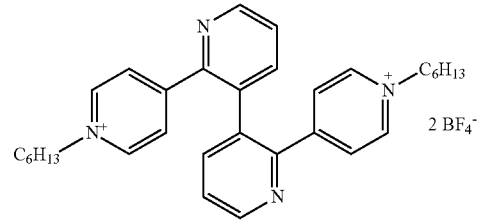 | −1.28 | * | * | * | 400 | pale yellow |
| III-5 | 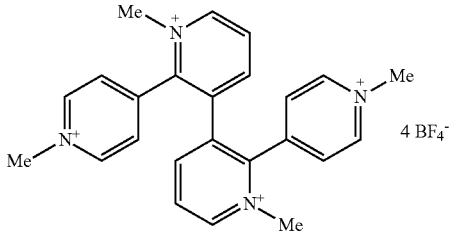 | −0.95 | −1.38 | 0.43 | * | 400 | orange |
| III-6 | 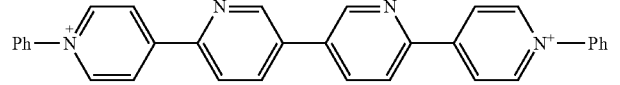 | −1.06 | * | * | −1.00 | 429 | yellow |

The invention claimed is:

1. An electrochromic compound of the formula (I):

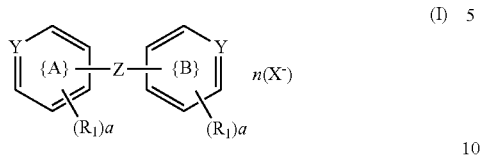

wherein:
Z is a 2,3 branched pyridinediyl radical or a pyridiniumdiyl radical;
each Y independently is N or ($^+$N—R$_2$)(X$^-$), wherein R$_2$ is a C$_1$-C$_{18}$ alkyl or an aryl;
each R$_1$ is independently selected from the group consisting of H, alkyl, alkoxy, alkylthio, haloalkyl, haloalkoxy, haloalkylthio, polyalkylenoxy, alkoxycarbonyl, aryl, and heteroaryl;
n is 1, 2, 3 or 4;
a is 4;
X– is a counterion; and
Z is not simultaneously bound in position 4 of cycle A and in position 4 of cycle B.

2. The compound according to claim 1, wherein the compound is represented by the formula (II):

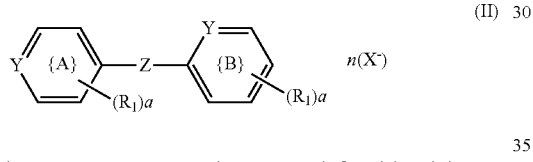

wherein Z, Y, R$_1$, X$^-$, a and n are as defined in claim 1.

3. The compound according to claim 1, wherein the compound is represented by the formula (III):

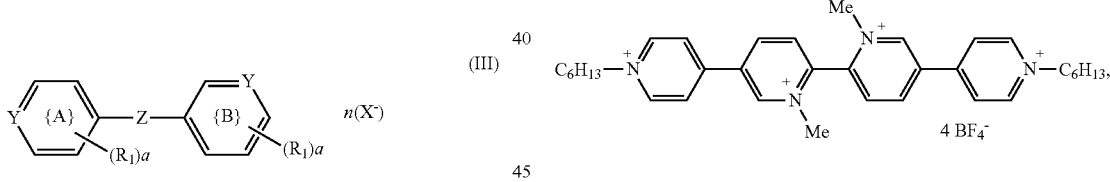

wherein Z, Y, R$_1$, X$^-$, a and n are as defined in claim 1.

4. The compound according to claim 1, wherein Z is a pyridiniumdiyl radical selected from the group consisting of:
1,4-branched pyridiniumdiyl radical;
2,3 branched N-alkylpyridiniumdiyl radical; and
2,5 branched pyridiniumdiyl radical.

5. The compound according to claim 1, wherein each Y independently is N or ($^+$N—R$_2$)(X$^-$), wherein with R$_2$ is a C$_1$-C$_8$ alkyl or an aryl.

6. The compound according to claim 1, wherein each R$_1$ independently is H, alkyl, or heteroaryl.

7. The compound according to claim 1, wherein Y in the cycle A and in the cycle B are N where n is 1, or wherein at least one Y is (+N—R$_2$)(X–) where n is 2, 3 or 4.

8. The compound according to claim 1, wherein the counterion X$^-$ is selected from the group consisting of halide, tetrafluoroborate, tetraphenylborate, hexafluorophosphate, nitrate, methanesulfonate, trifluoromethane sulfonate, p-toluenesulfonate, hexachloroantimonate, bis(trifluoromethanesulfonyl)imide, perchlorate, acetate and sulfate.

9. The compound according to claim 1, wherein the compound is selected from the group consisting of:

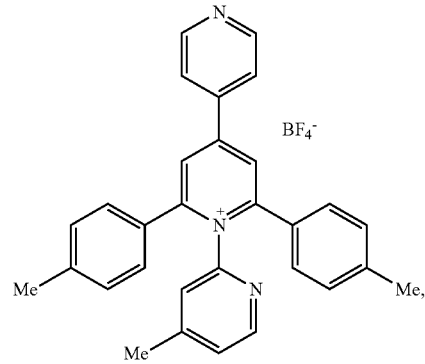

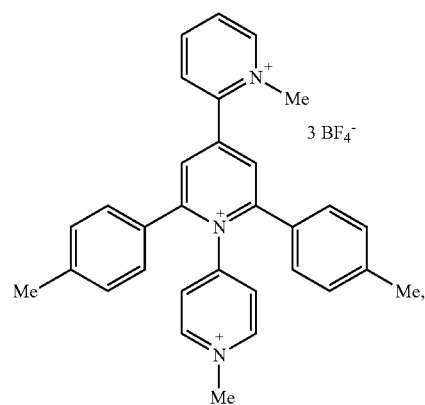

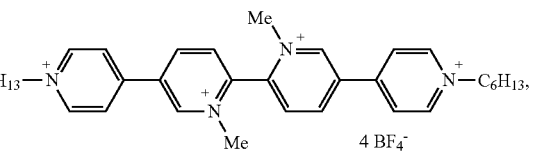

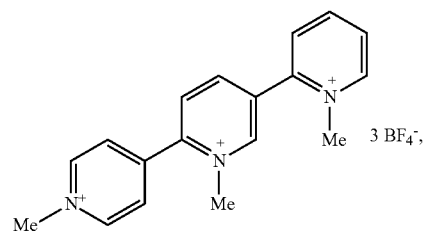

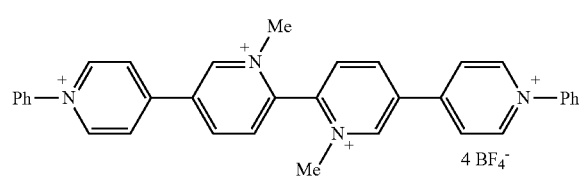

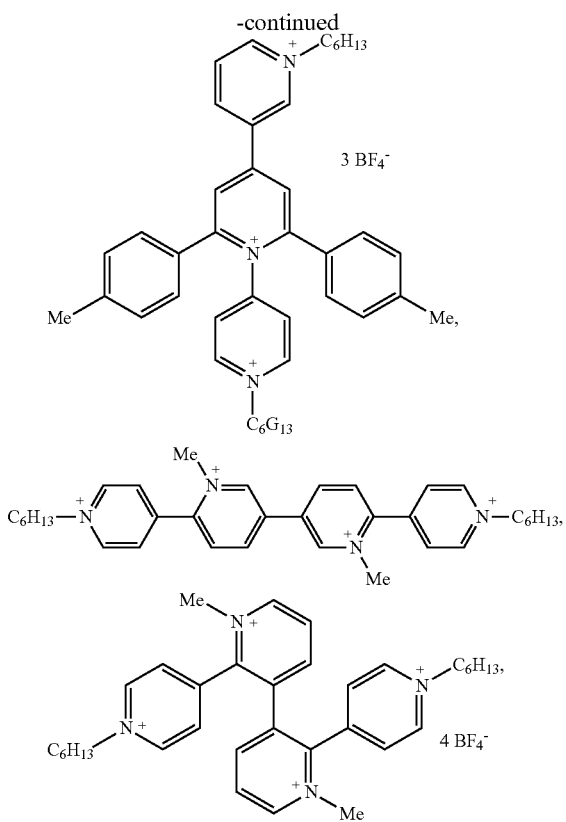

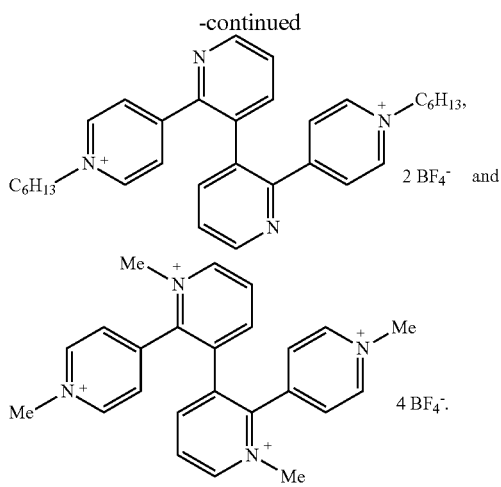

10. An electrochromic composition comprising at least one compound according to claim 1.

11. The electrochromic composition according to claim 10, wherein the composition further comprises a host medium.

12. An electrochromic device comprising the compound according to claim 1.

13. The electrochromic device according to claim 12, wherein the electrochromic device is selected from the group consisting of an optical article, a visor, a mirror, a head mounted device and a display.

* * * * *